United States Patent [19]

Sekino et al.

[11] Patent Number: 5,078,144
[45] Date of Patent: Jan. 7, 1992

[54] SYSTEM FOR APPLYING ULTRASONIC WAVES AND A TREATMENT INSTRUMENT TO A BODY PART

[75] Inventors: Naomi Sekino; Shuichi Takayama, both of Hachioji; Masakazu Gotanda, Kanagawa; Koichiro Ishihara, Hachioji; Naoki Uchiyama, Hachioji; Nobuhiko Watanabe, Hachioji; Masaaki Nakazawa, Hino; Tsuguhisa Sasai, Sagamihara; Tsutomu Okada, Kunitachi; Takeo Haneda; Masaaki Hayashi, both of Hachoji, all of Japan

[73] Assignee: Olympus Optical Co. Ltd., Japan

[21] Appl. No.: 366,162

[22] Filed: Jun. 14, 1989

[30] Foreign Application Priority Data

| Aug. 19, 1988 | [JP] | Japan | 63-206074 |
| Aug. 19, 1988 | [JP] | Japan | 63-206075 |
| Oct. 5, 1988 | [JP] | Japan | 63-252464 |
| Oct. 6, 1988 | [JP] | Japan | 63-131494[U] |
| Oct. 6, 1988 | [JP] | Japan | 63-253348 |

[51] Int. Cl.⁵ .............................................. A61B 17/22
[52] U.S. Cl. .......................... 128/660.03; 128/24 EL
[58] Field of Search .............. 128/653 R, 654, 660.03, 128/662.05, 804, 24 AA, 24 EL; 600/2; 604/22

[56] References Cited

U.S. PATENT DOCUMENTS

| 4,758,596 | 7/1988 | Thistle et al. . | |
| 4,771,787 | 9/1988 | Wurster et al. | 128/24 EL |
| 4,781,677 | 11/1988 | Wilcox . | |
| 4,803,995 | 2/1989 | Ishida et al. | 128/24 EL |
| 4,825,851 | 5/1989 | Cocks et al. | 128/24 A |
| 4,845,125 | 7/1989 | Geier | 128/24 A |
| 4,917,095 | 4/1990 | Fry et al. | 128/24 A |
| 4,955,366 | 9/1990 | Uchiyama et al. . | |
| 4,958,639 | 9/1990 | Uchiyama et al. . | |

FOREIGN PATENT DOCUMENTS 2942405  4/1981  Fed. Rep. of Germany .................. 128/662.05

Primary Examiner—Ruth S. Smith
Attorney, Agent, or Firm—Ostrolenk, Faber, Gerb & Soffen

[57] ABSTRACT

An ultrasonic treatment system for conducting treatment by converging ultrasonic waves which are generated outside of a body to a part to be treated in the body comprising an ultrasonic wave generator for generating the ultrasonic waves to be converged to the part to be treated; and an insertion tube connected to the ultrasonic wave generator for guiding an instrument, such as a syringe, employed to introduce and/or return a treatment material to the body.

3 Claims, 20 Drawing Sheets

SYSTEM FOR APPLYING ULTRASONIC WAVES AND A TREATMENT INSTRUMENT TO A BODY PART

BACKGROUND OF THE INVENTION

The present invention relates to an ultrasonic treatment method and system for the same and in particular to an ultrasonic treatment method and system for the same in which a treatment material is introduced to a part to be treated and ultrasonic wave is converged thereto.

Various ultrasonic treatment systems for irradiating a part to be treated with ultrasonic wave to conduct treatment have heretofore been proposed. However an ultrasonic treatment system which is capable of conducting more effective and fast treatment is demanded.

It is therefore an object of the present invention to provide an ultrasonic treatment system which is capable of conducting effective and fast treatment.

SUMMARY OF THE INVENTION

In an aspect of the present invention, there is provided an ultrasonic treatment system for conducting treatment by converging ultrasonic waves which are generated outside of a body to a part to be treated in the body comprising means for generating the ultrasonic waves to be converged to the part to be treated, and means for introducing and/or returning a treating material to the body.

In another aspect of the present invention, there is provided an ultrasonic treatment system comprising means for locating the position of a calculus formed in a body, first ultrasonic wave irradiating means for destroying the calculus by irradiating the calculus with an ultrasonic wave beam, second ultrasonic wave irradiating means for promoting the dissolution of said calculus by irradiating the calculus with ultrasonic wave, and means for moving the focus of said ultrasonic wave beam.

In a further aspect of the present invention, there is provided an ultrasonic treatment system comprising means for generating ultrasonic waves outside of a body to converge the same toward a part to be treated in the body and means for changing the driving frequency of an ultrasonic oscillator of said ultrasonic wave generator to change the convergence of the ultrasonic wave at a converging point.

In a further aspect of the present invention, there is provided an ultrasonic treatment method comprising, converging ultrasonic waves which are generated from an ultrasonic oscillator outside of a body toward a part to be treated in a body and changing the driving frequency of the ultrasonic wave oscillator to change the converging manner at the convergence point.

BRIEF DESCRIPTION OF THE DRAWINGS

The above-mentioned and other objects and features of the present invention will become more apparent by reading the following description with reference to the drawings in which.

DESCRIPTION OF THE PREFERRED EMBODIMENTS

Now an embodiment in which means is provided for guiding a treatment instrument such as piercing needle which passes through ultrasonic generating means and ultrasonic transmitting medium means will be described.

Figure 1:
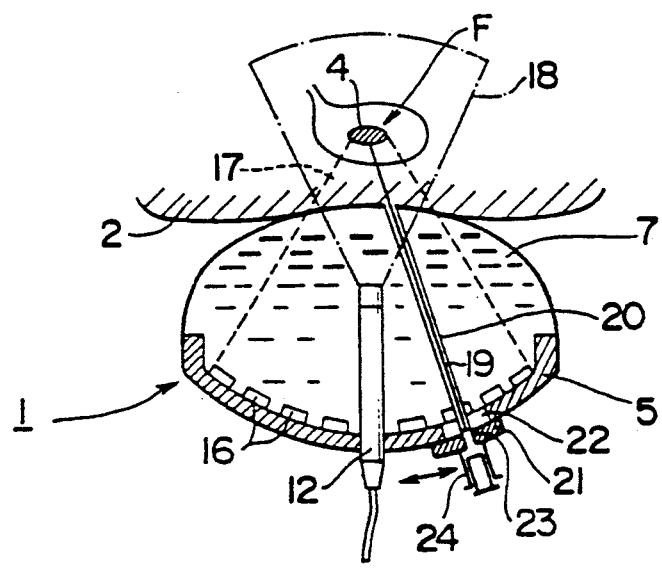
FIG. 1 is an enlarged sectional view showing a main part of a first embodiment of an ultrasonic treatment system of the present invention.
Figure 2:
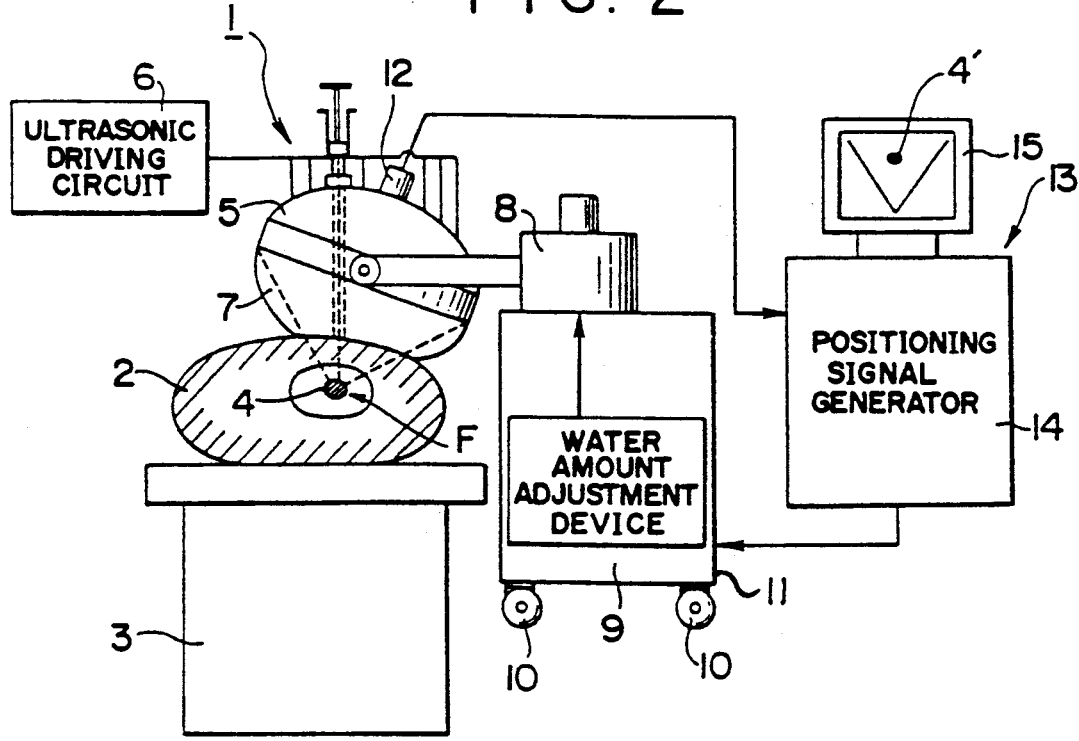
FIG. 2 is schematic view showing a whole ultrasonic treatment system emboding the present invention.

Referring now to FIGS. 1 and 2, reference numeral 1 represents an ultrasonic treatment system, 2 a human body, 3 a therapeutic bed, 4 a calculus in the human body, and 5 a high power ultrasonic wave generator having a multiplicity of ultrasonic oscillating elements juxtaposed on the inner side of a spherical shell. The generator 5 is driven by an ultrasonic wave driving circuit 6 to converge the high power ultrasonic waves upon a focus F of the spherical shell. A water bag 7 made of a soft resin which is filled with an ultrasonic transmitting medium such as water is disposed between the high power ultrasonic wave generator 5 and the human body 2. The high power ultrasonic wave generator 5 is rotated and displaced in three-dimensional direction by means of moving device 8 using, for example, electromagnetic motor or hydraulic unit. The moving device 8 is disposed on the upper face of a main body 9 of an ultrasonic treatment instrument which is movable by means of casters 10. A water amount adjusting apparatus 11 which charges and discharges an ultrasonic wave transmitting medium such as water to and from the water bag 7 is disposed inside of the main body 9. A positioning device 13 detects the position of the calculus 4 in a human body 2 by means of position detecting ultrasonic oscillating element 12 mounted on the generator 5 at the approximate center thereof. The generator 5 can be moved by the positioning device 13 in response to a positioning signal output from a positioning signal generator 14 which forms part of the positioning device 13 so that the point of convergence of the ultrasonic waves transmitted from the generator 5 coincides with the position of the calculus 4.

The positioning signal generating circuit 14 has the function of transmitting and receiving signals to and from the oscillating element 12 and the function for processing the received signal. The circuit 14 outputs to a display 15 an ultrasonic tomographic signal which is generated by signal-processing to display an ultrasonic tomographic image. The positioning device 13 having this circuit 14 is provided with position assigning means, such as a write pen, a cursor key in a keyboard, a mouse or joy stick, which assigns the position on a display face of the display 15. A desired position of an indication marker on a display face is assigned by manipulating the position assigning means. By presetting the marker position on the position of the calculus 4' displayed on a display face, the spatial position of the assigned position is detected. A positioning signal representative of how far the current position of the converging point should be moved is generated in response to this detection. The positioning signal is input to the moving device 8 to drive the moving motor for displacing the high power ultrasonic wave generator 5. Simultaneously with this, the water amount adjusting device 11 adjusts the amount of water in the water bag 7 to prevent the formation of an air gap between the water bag 7 and the human body 2.

As shown in FIG. 1, the high power ultrasonic wave generator 5 in the present embodiment has a multiplicity of ultrasonic wave oscillating elements 16 disposed on the inner side of the spherical shell and is closed by the water bag 7 filled with the ultrasonic transmitting medium such as water. Strong ultrasonic waves which are generated from the ultrasonic oscillating elements 16 transmit through an area shown with dotted lines to converge to a focus F of the spherical shell. The high power ultrasonic wave generator 5 is provided with a position detecting ultrasonic oscillating element for locating a part to be treated such as a calculus at a position along a central axis thereof. An ultrasonic tomographic image in an area represented by chain lines 18 is obtained from this oscillating element 12. An insertion tube 20 which forms a guide passage into which a syringe needle 19 or the like is provided so that it passes through the water bag 7 and the high power ultrasonic wave generator 5. The insertion pipe 20 has an end secured to the surface of the water bag 7 and the other end secured to an insertion tube connector 21. The connector 21 is slidable along the outer surface of the spherical shell of the high power ultrasonic wave generator 5. The spherical shell is provided with a guide hole 22 so that the insertion pipe 20 is movable through a gap of an ultrasonic oscillating element 16. The front end of the syringe 24 can be firmly adapted into the insertion opening 23 of the insertion connector 21.

Figure 3:
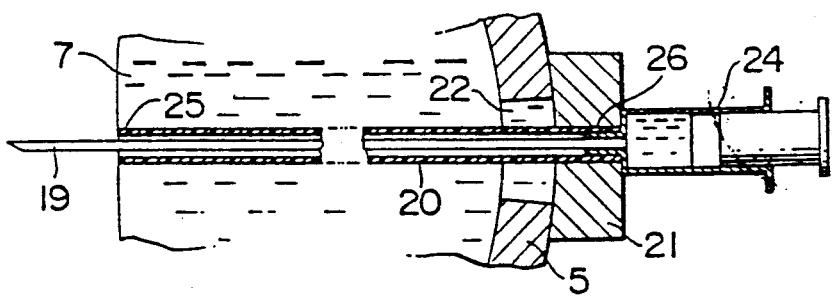
FIGS. 3 and 4 are enlarged sectional views showing an insertion tube shown in FIG. 1 into which a syringe is inserted.
Figure 4:
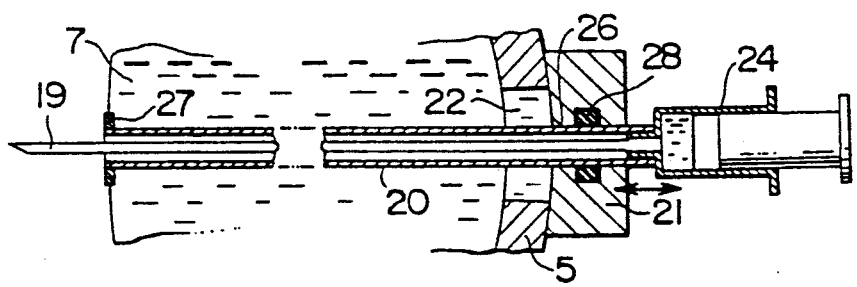

Referring now to FIGS. 3 and 4, there are shown the details of the insertion tube 20. The insertion tube 20 is made of a flexible tube which is extensible so that it can follow the slide of the insertion tube 20 and upward and downward movement of the water bag 7. As shown in FIG. 3, the insertion tube 20 is bonded to the water bag 7 at the connector 25 and is bonded to the insertion tube connector 21 at the inner peripheral surface 26 thereof. When the insertion tube 20 is made of a rigid tube as shown in FIG. 4, the insertion tube 20 is secured to the water bag 7 through a connecting member 27. Watertightness between the tube 20 and connector 21 is maintained by means of water proof member 28 such as O ring and the tube 20 is slidable in a direction as shown by an arrow in the drawing.

Figure 5:
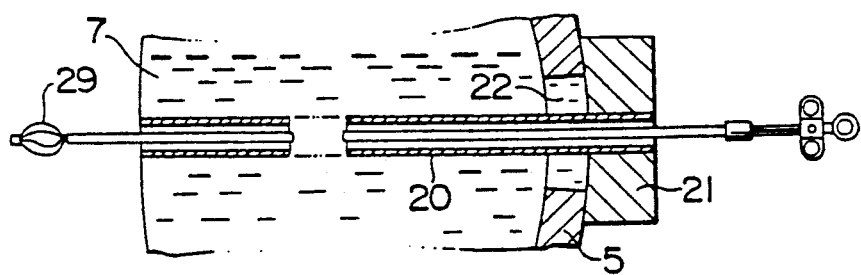
FIG. 5 is an enlarged sectional view showing an insertion tube shown in FIG. 1 into which a basket forceps is inserted.

FIG. 5 is the enlarged sectional view showing that a treatment instrument, such as basket forceps 29, other than syringe needle 19, may be inserted into the insertion tube 20. Since the insertion tube 20 provides the means of which any treatment instrument can be inserted between the water bag 7 and the high power ultrasonic wave generator 5, an ultrasonic wave transmission rod having a very small diameter for an ultrasonic lithorite using mechanical vibration and a probe for an lithorite which generates electric-water pressure impact wave can be inserted to conduct direct lithotresis.

Figure 6:
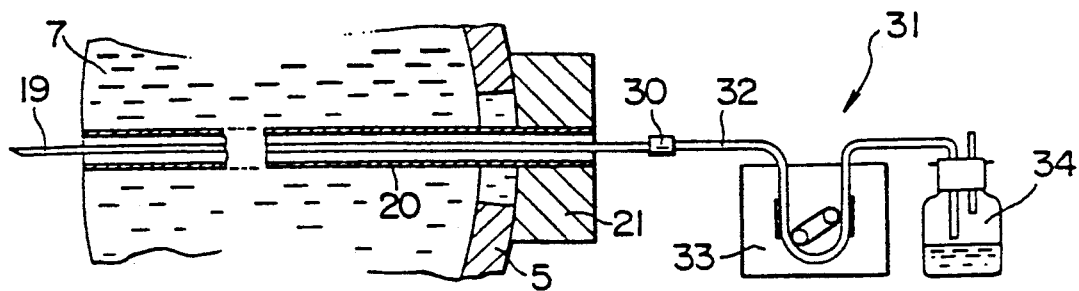
FIG. 6 is an enlarged sectional view showing an insertion tube into which a syringe needle connected with a water feeding/sucking pump is inserted.

Referring now to FIG. 6, there is shown a case in which the syringe needle 19 is connected to a feeding-/sucking pump 31. The syringe needle 19 is connected to a tube 32 through an adapter 30 and the tube 32 is connected through a roller pump 33 to a reservoir which stores a liquid or sucked material.

Operation of the ultrasonic treatment system 1 in the present embodiment will be described. The main body 9 of the ultrasonic treatment system is first transported to a position near the therapeutic bed 3 by casters 10 as shown in FIG. 2. The high power ultrasonic generator 5 is then rotated and displaced in three-dimensional direction by means of moving device 8 to a position where the water bag 7 is in contact with the human body 2. The convergence point of the ultrasonic wave transmitted from the high power ultrasonic generator 5 is brought into coincidence with the position of the calculus 4 by means of the positioning device 13. While the position of the calculus 4' and other organs on a display face of the monitor display 15 is monitored, the syringe needle 19 is inserted into the insertion tube 20 to advance the tip end of the needle 19 to a position near the calculus 4 by piercing the skin of the human body 2. The insertion tube connector 21 is slidable along the outer surface of the spherical shell to change the direction of piercing so that the needle 19 will not pierce an organ other than a target organ, for example, the cholecyst. A suitable amount of lithotriptic is injected into the cholecyst by manipulating the syringe 24. After injection of the lithotriptic, the ultrasonic driving circuit 6 is driven to irradiate the calculus 4 with high power ultrasonic waves. The calculus 4 is then destroyed by the coaction of the lithotriptic and ultrasonic waves. The dissolved content is recovered through the needle 19 by the syringe 24. If complete dissolution does not take place by one treatment, the above-mentioned operation will be repeated. Alternatively, a lithotrite treatment instrument, such as basket forceps 29 shown in FIG. 5, is inserted to destroy or break the calculus 4 into pieces less than a given dimension and then the calculus pieces may be dissolved by the injection of lithotriptic and irradiation of ultrasonic wave. Injection of the lithotriptic and recovery of dissolved content can also be accomplished by means of feeding/sucking pump 31 (refer to FIG. 6) as well as the syringe 24.

Access to a target organ can be accomplished in a reliable manner without piercing other organs when the syringe needle 19 and other treatment instruments are inserted since the insertion tube 20 is movable in accordance with the ultrasonic treatment system in the present embodiment. Remarkable effects such as good promotion of dissolution of biliary calculus may be obtained since an auxiliary therapy by treatment instruments other than syringe needle for injecting lithoptriptic is possible due to a fact that the insertion tube 20 can guide various treatment instruments. Lithotripic, calculus dissolving agents which may be used in the present invention includes tert-butyl methyl ether, monooctanoin, d-limonene, dimethyl sulfoxide, sodium hexamethaphosphate, sodium ethylenediamine tetraacetate and any combination thereof.

Although the ultrasonic treatment system has been described as a system for promoting the dissolution of calculus such as biliary calculus in the above-mentioned embodiment, the ultrasonic treatment system of the present invention may be used for other treatments, for example, hyperthermia for curing cancer or tumor or ultrasonic PDT method, as well as promotion of calculus dissolution. In the former hyperthermic method, a material which generates heat on being irradiated with supersonic wave, for example material which is not harmful to the living body such as silicone rubber, polyethylene, acrylic resin, tetrafluoroethylene is injected to a part to be treated in lieu of lithotriptic. In the latter ultrasonic PDT method, a photo-susceptible material such as hematoporphirine derivatives and pheophorbide a is injected.

On therapy of cancer or tumor, a medicine for curing them may be used together with the material used for hyperthermia and/or the photo-susceptible material.

Figure 7:
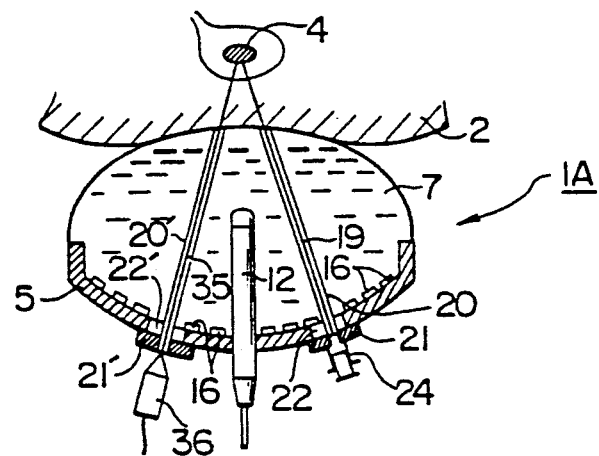
FIG. 7 is an enlarged sectional view showing a second embodiment of an ultrasonic treatment system of the present invention.

Referring now to FIG. 7, there is shown a second embodiment of the present invention.

An ultrasonic treatment system 1A of the present embodiment is substantially identical with the ultrasonic treatment system 1 shown in FIG. 1 excepting that one or more insertion tubes 20' which pass through the water bag 7 and the generator 5 to form a guiding passage for treatment instruments is provided in such a manner that a position detecting ultrasonic oscillating element 12 is disposed between both insertion tubes, 20 and 20'. The insertion tube 20' is connected to the water bag 7 and the high power ultrasonic generator 5 at a different position, but has a structure identical with the insertion tube 20. That is, the insertion tube 20' has one end connected to the surface of the water bag 7 and the other end secured to the insertion tube connecor 21'. The connector 21' is slidable along the outer surface of the spherical shell of the high power ultrasonic wave generator 5. A guide hole 22' is provided in the generator 5 so that the insertion tube 20' is movable in a spacing between ultrasonic oscillating element 16. The syringe 24 having the needle 19 is inserted into the insertion tube 20 and an ultrasonic lithotrites 36 having a ultrasonic wave transmiting rod 35 with a very small diameter is inserted into the insertion tube 20' in FIG. 7. This structure makes it possible to combine various treatment instruments. It is of course possible to provide more than two insertion tubes.

Since the whole structure of the ultrasonic treatment system 1A in the present embodiment is identical with the first embodiment shown in FIGS. 1 and 2, operation until the lithotriptic is injected by means of injection needle 19 is identical with that in the first embodiment. If the effect of dissolution of calculus is insufficient, the front end of the ultrasonic transmitting rod 35 is advanced in the same manner as the syringe needle 19 and the lithotrite 36 is driven to destroy calculus. After the calculus has been destroyed into calculus pieces, the ultrasonic driving circuit 6 is driven to irradiate the calculi 4 with high power ultrasonic waves. After the calculi 4 have been dissolved, the dissolved content is recovered through the needle 19 by means of syringe 24. The auxiliary technique for destroying calculus is not limited to only such an ultrasonic lithorite 36. Other basket forceps 29 and lithotrite using electro-hydraulic pressure impact wave may be used. The syringe needles 19 which are connected to the water feeding sucking pumps 31 shown in FIG. 6 are inserted into the insertion tubes 20, 20' to conduct injection of lithotriptic simultaneously with recovery of the dissolved content. Calculus dissolving treatment with the ultrasonic irradiation can be conducted while the medical fluid is circulated in such a manner.

Since a plurality of guide passages for insertion of treatment instruments are provided in the present embodiment of the ultrasonic treatment system 1A, ultrasonic lithotresis can be realized simultaneously with auxiliary therapy by injection of lithotriptic and recovery of dissolved biliary calculus, resulting in an improved therapeutic effect.

Figure 8:
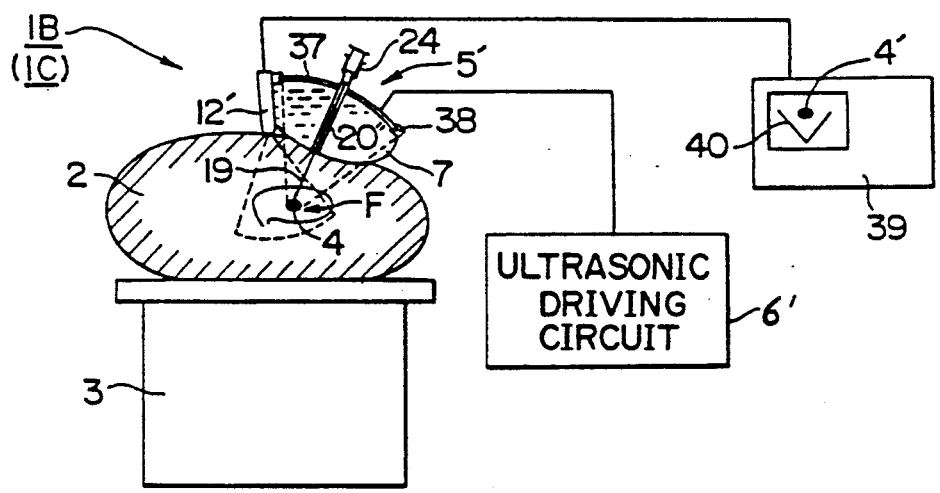
FIG. 8 is a schematic view showing an ultrasonic treatment system used in implementing in a third and a fourth embodiment of the present invention.

Referring now to FIG. 8, there is shown a system for implementing third and fourth embodiments of the present invention. A high power ultrasonic generator 5' comprises a single concave oscillating element 37. The element 37 is driven by an ultrasonic driving circuit 6' so that the generated ultrasonic waves are converged to a focus F. The concave oscillating element 37 is secured to a main body of the high power ultrasonic generator by means of element securing ring member 38. A water bag made of a soft resin which is filled with water is disposed between a human body 2 and the generator 5'. An insertion tube 20" is provided which passes through a part of partial spherical surface of the concave oscillating element 37 and the water bag 7 to form a guide passage into which a treatment instrument is inserted. The insertion tube 20" has an end at the side of the element 37 which can slide along the spherical surface of the concave oscillating element 37. A position detecting ultrasonic oscillating element 12' is disposed on a part of the outer periphery of the generator 5'. The central axis of a sector shaped observation range coincides with the focus F of the generator 5'. The ultrasonic oscillating element 12' is connected to an ultrasonic observing device 39 to display an ultrasonic tomographic image on a monitor display 40.

Figure 9:
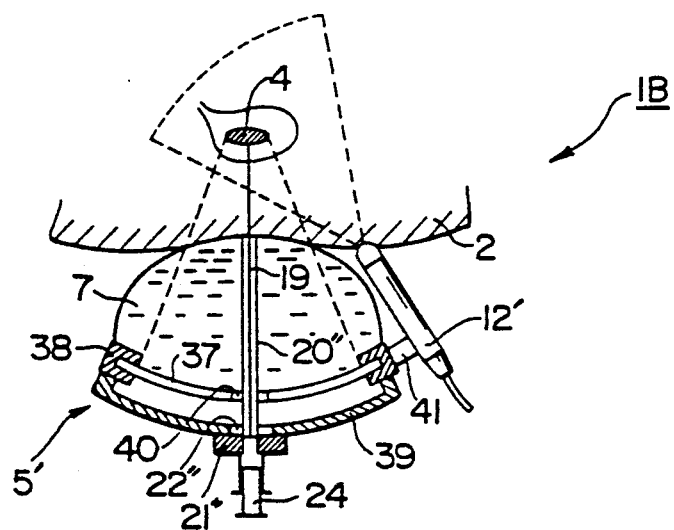
FIG. 9 is an enlarged sectional view showing the third embodiment of an ultrasonic treatment system of the present invention.

Referring now to FIG. 9, there is shown the third embodiment of an ultrasonic treatment system 1B which includes a high power ultrasonic generator 5'. The generator 5' is provided with a concave oscillating element 37 inside thereof. The generator 5' further includes oscillating element securing member 38, a spherical supporting member 39 and a water bag 7 filled with an ultrasonic transmitting medium such as water. An insertion tube 20" which passes through the water bag 7 and the supporting member 39 is disposed therebetween. The insertion tube 20" has at the side of the supporting member 39 an end secured to an insertion tube connector 21". The connector 21" is slidable along the outer spherical surface of the supporting member 39. Guide holes 22" and 40 are provided at the supporting member 39 and a part of the spherical surface of the concave oscillating element 37 respectively so that the insertion tube 20" is movable. A position detecting ultrasonic oscillating element 12' is detachably mounted on a part of the outer periphery of the generator 5' by means of mounting member 41.

Operation of the ultrasonic treatment system 1B in the present embodiment will be described. The converged ultrasonic wave generator 5' is disposed to face to the human body 2 through the water bag 7. Then the position detecting ultrasonic oscillating element 12' is pressed to abut to the human body 2 to observe the inside of the body. The operation for moving and fixing the converged ultrasonic wave generator 5' is conducted manually or by a simple positioning apparatus (not shown). The ultrasonic tomographic image representing the inside of the body is displayed on a monitor display 40 (refer to FIG. 8). A calculus in a part to be treated is searched to be moved to a position at which the calculus is displayed on the monitor. Then, the insertion tube connector 21" is slid to move the insertion tube 20" in such a direction that the syringe needle 19 will not pierce organs other than the cholecyst if there is a biliary calculus. After the syringe needle 19 is caused to pierce the part near the calculus 4, the syringe 24 is operated to inject a lithotriptic into the part around the calculus. Thereafter the ultrasonic driving circuit 6'(refer to FIG. 8) is driven to irradiate the calculus with the converged high power ultrasonic wave. After dissolution of the calculus, the dissolved content is recovered via the needle 19 by means of syringe 24. If complete dissolution of the calculus is not realized by one treatment, the above operation is repeated, or lithotresis using various treatment instruments, such as basket forceps, ultrasonic lithotrite, electro-hydraulic pressure impact wave apparatus will be tried as an auxiliary therapy.

Since the converged ultrasonic wave generator 5' uses a single concave oscillating element 37, the system is compact in size. Accordingly an operator can easily manipulate the system.

Figure 10:
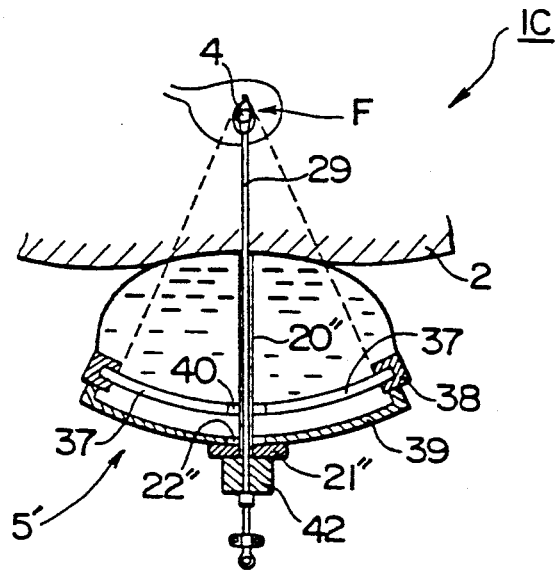
FIG. 10 is an enlarged sectional view showing the fourth embodiment of an ultrasonic treatment system of the present invention.

Referring now to FIG. 10, there is shown a fourth embodiment of an ultrasonic treatment system 1c. A converged ultrasonic wave generator 5' in the present embodiment is substantially identical with that shown in FIG. 8 excepting that the former is different from latter in that the former is provided with a member 42 which fixes the position of a treatment instrument such as basket forceps 29. The tip end of the forceps coincides with a point of convergence of the generator 5' when the basket forceps 29 is fixed.

Operation of the ultrasonic treatment system 1c in the present embodiment will be described. Since the whole of the system is formed as shown in FIG. 8, operation until the lithotriptic is injected using a needle 19 is identical with that in the third embodiment. Then a treatment instrument such as basket forceps 29 is advanced in the same manner as the needle 19 so that the tip end will be positioned in the vicinity of the calculus to grip the calculus with the basket. After the basket forceps 29 has been fixed by a treatment fixing member 42, the generator 5' is driven to irradiate the calculus with high power ultrasonic waves.

Since the calculus 4 is fixed to the point of convergence of the high power ultrasonic waves by the basket forceps 29 in accordance with the fourth embodiment, the irradiating ultrasonic wave will positively impinge upon the calculus 4 without missing it. Accordingly therapeutic effect is further improved.

Figure 11:
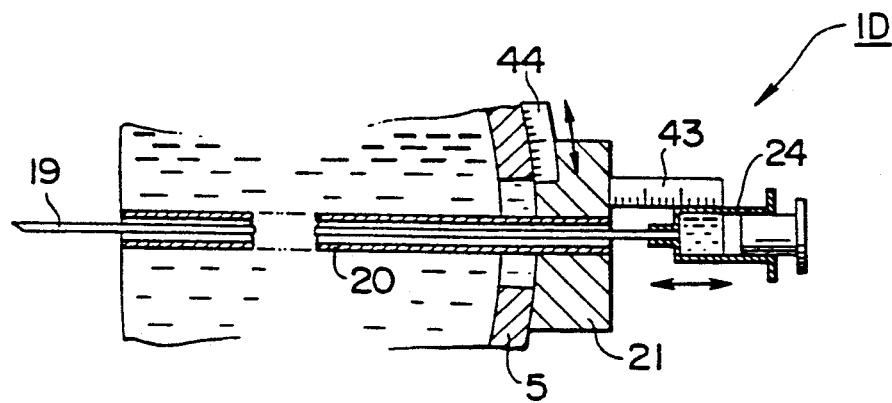
FIG. 11 is an enlarged sectional view showing an insertion tube in a fifth embodiment of an ultrasonic treatment system.

Referring now to FIG. 11, there is shown the detailed structure of an insertion tube 20 in a fifth embodiment of an ultrasonic treatment system 10. A scale plate 43 indicates the amount of slide of a syringe needle 19 and a syringe 24. Angle indicating plate 44 indicates the amount of slide of an insertion tube connector 21, that is, the amount of the movement of the insertion tube 20.

When the treatment instrument such as syringe needle 19 pierces a part in the vicinity of a calculus which is a target in the embodiment of the ultrasonic treatment system 1D, it is possible to operate the system so that the length and direction in which the needle 19 pierces is preset in accordance with the readings on the scale plate 43 and the angle indicating plate 44 after the length to the target and the angle has been confirmed by the ultrasonic observing device. Therefore it is possible to introduce the treatment instrument to a target position.

In the afore-mentioned embodiments, means for guiding the treatment instrument such as piercing needle, that is, insertion passage including insertion tube 20, 20', or 20" is disposed in such a manner that it passes through the ultrasonic wave generator 5, 5' which an ultrasonic wave generating means and the water bag 7 which is an ultrasonic wave transmitting medium means. Such a structure is slightly complicated.

Therefore an embodiment of the present invention will be described in which means for guiding a treatment instrument is provided which does not passes through ultrasonic generating means and ultrasonic transmitting means.

Figure 12:
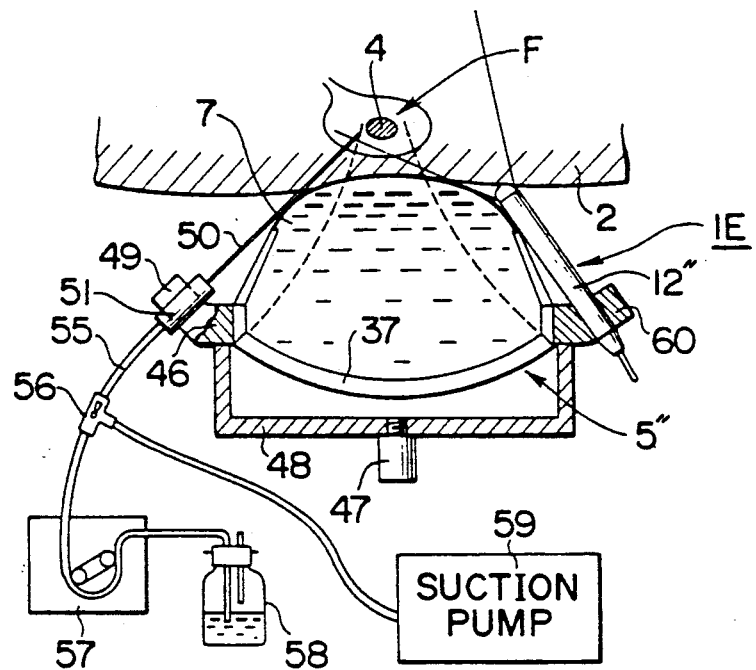
FIG. 12 is an enlarged sectional view showing a sixth embodiment of an ultrasonic treatment system of the present invention.
Figure 13:
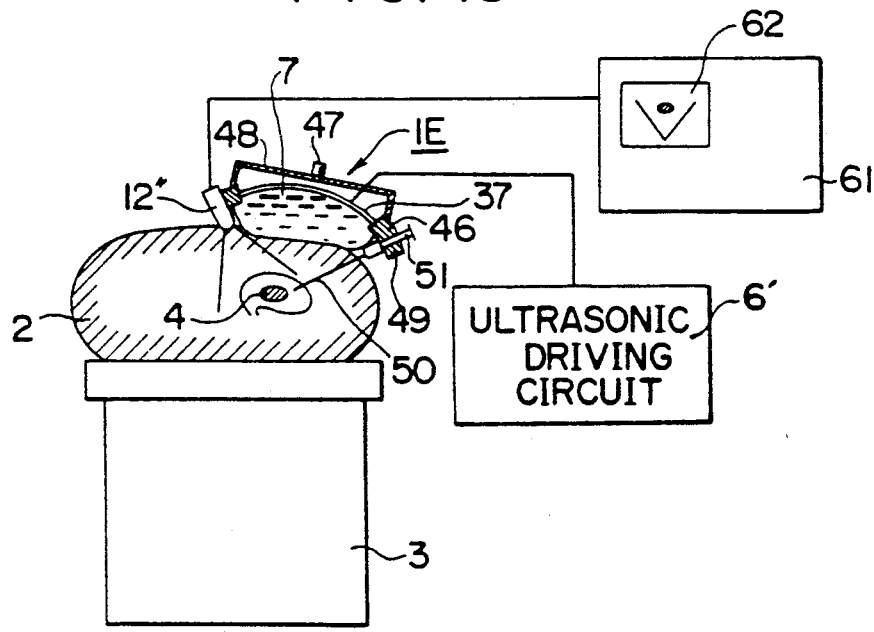
FIG. 13 is a schematic view showing a whole structure of an ultrasonic treatment system including the sixth embodiment.

Referring now to FIGS. 12 and 13, there is shown a sixth embodiment of an ultrasonic treatment system 1E of the present invention. A converged ultrasonic wave generator 5" comprises a concave oscillating element or a multiplicity of ultrasonic oscillating means 37. The generator 5" has a water bag 7 on the ultrasonic wave generating face. The generator 5" is mounted on an annular support 46 at the outer periphery thereof. The annular support 46 is firmly secured to a holding frame 48, which is then supported by a supporting shaft 47. The oscillating element 37 of the generator 5" is driven by an ultrasonic driving circuit 6'. The generated ultrasonic waves transmit through the water bag 7 disposed between the human body 2 and the generator 5" and are converged to a focus F located at a calculus 4. The positioning of the generator 5" to the human body 2 on the therapeutic bed 3 is carried out manually by an operator or by position control means including a motor and the like.

Figure 14:
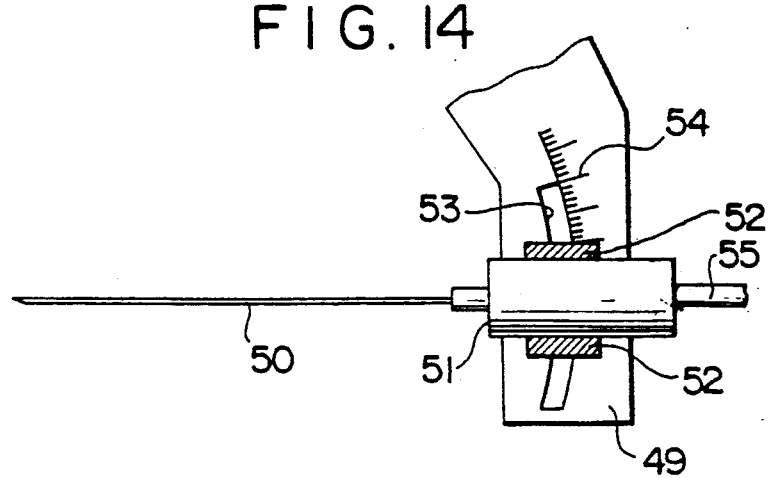
FIG. 14 is an enlarged plan view showing means for guiding a treatment device in the sixth embodiment.

An outwardly projecting mount 49 for guiding treatment instruments is provided at a part of the annular support 46. As best seen in FIG. 14, the instrument guiding mount 49 comprises a holder 52 for detachably mounting medical liquid injecting instruments including a syringe needle 50 and a syringe 51 as shown in FIG. 14. The holder 52 is slidably disposed on a guide rail 53. Angle indicating graduation is engraved along the guide rail 53 so that piercing direction of the needle 50 of the syringe 51 held by the holder can be read by the graduation 54.

Injection of a medical liquid from the syringe needle 50 to the cholecyst is conducted from a liquid bottle 58 by means of roller pump 57 which is connected to the syringe 51 via a tube 55 and a three-directional valve 56 as shown in FIG. 12. Recovery of the dissolved calculus is conducted by switching the three-directional valve 56 and operating the suction pump 59.

The support 46 is formed with a probe holder 60 which projects outwardly at a part thereof. An ultrasonic observing probe including position detecting ultrasonic oscillating element 12" is detachably held by the holder 60. The held oscillating element 12" is disposed so that the focus F of the generator 5" is located on the central axis of the sector observing range. The oscillating element 12" is connected to an ultrasonic observing device 61 to display an ultrasonic tomographic image on a monitoring display 62. The ultrasonic observing probe can be detached from the holder 60 and be solely used.

Since the treatment instrument guiding means does not pass through the generator 5" and the water bag 7 and is provided at the outer periphery of the generator 5" in the ultrasonic treatment system 1E of the present invention, the structure of the system is simplified and the treatment instrument can be precisely introduced.

Although single medical liquid injection means comprising the syringe needle 50 and the syringe 51, that is, single treatment instrument guiding means is provided, a plurality of guiding means may be provided at the outer periphery of the support 46. Thus, injection of medical liquid may be conducted simultaneously with recovery of the dissolved calculus.

Figure 15:
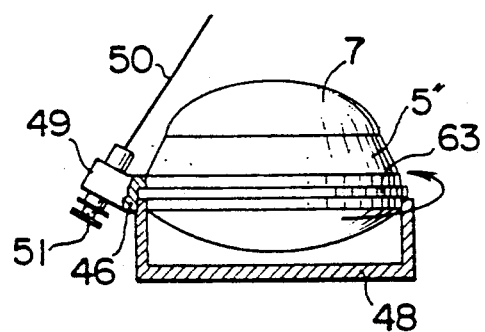
FIG. 15 is a schematic view showing a modified means for guiding a treatment device in the sixth embodiment.

If the treatment instrument guiding means 49 is disposed on the guide rail 63 which is formed along the outer periphery of the support 46 in such a manner as shown in FIG. 15 that it can slide along the rail 63 in a direction shown by an arrow, piercing of the needle 50 could be conducted at an optimum position and in an optimum direction upon basis of the observed image from the position detecting ultrasonic oscillating element 12".

If the probe holder 60 is slidable along the guide rail 63, piercing of the needle 50 could be conducted at an optimum position in response to a tomographic image obtained from the oscillating element 12".

It is possible to provide the afore-mentioned embodiments with a pressure sensor at the tip end of the treatment instrument, such as a syringe needle, to measure the pressure in the cholecyst, a mechanism for adjusting the amount of the medical liquid to be injected, a thermal sensor at the tip end of the treatment instrument to measure the temperature elevation in the cholecyst due to ultrasonic wave irradiation, and a mechanism for controlling the timing, power, etc. of the ultrasonic irradiation. Provision of these means provides more effective ultrasonic treatment system.

In accordance with the present invention, various treatment instruments other than a syringe needle can be precisely inserted without any trouble for the therapy of any disease and recovery of dissolved calculus can be very easily conducted and fast treatment can be conducted.

Figure 16:
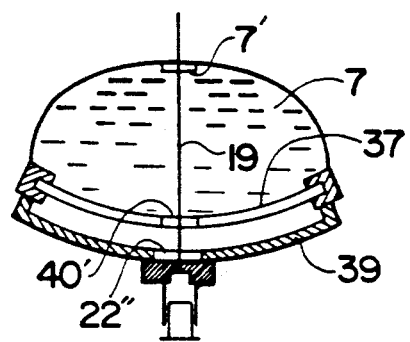
FIG. 16 is a schematic view showing a main part of a seventh embodiment of an ultrasonic treatment system of the present invention.

Referring now to FIG. 16, there is shown a seventh embodiment. This embodiment is substantially identical with the third and fourth embodiments shown in FIG. 9. However it is different from the third embodiment in that guiding means is not an insertion tube and comprises self-sealing material 22''', 40' and 7' which are respectively provided at positions of guide holes 22" and 40' and a part of the water bag membrane located on a line extending through holes 22" and 40. The self-sealing material is made of silicone rubber having a thickness of about 5 mm. A syringe needle 19 passes through the sealing material while keeping watertightness. Even if the needle 19 is removed from the sealing material, the pierced hole will close by itself to prevent the leakage of water in the water bag 7.

Figure 17:
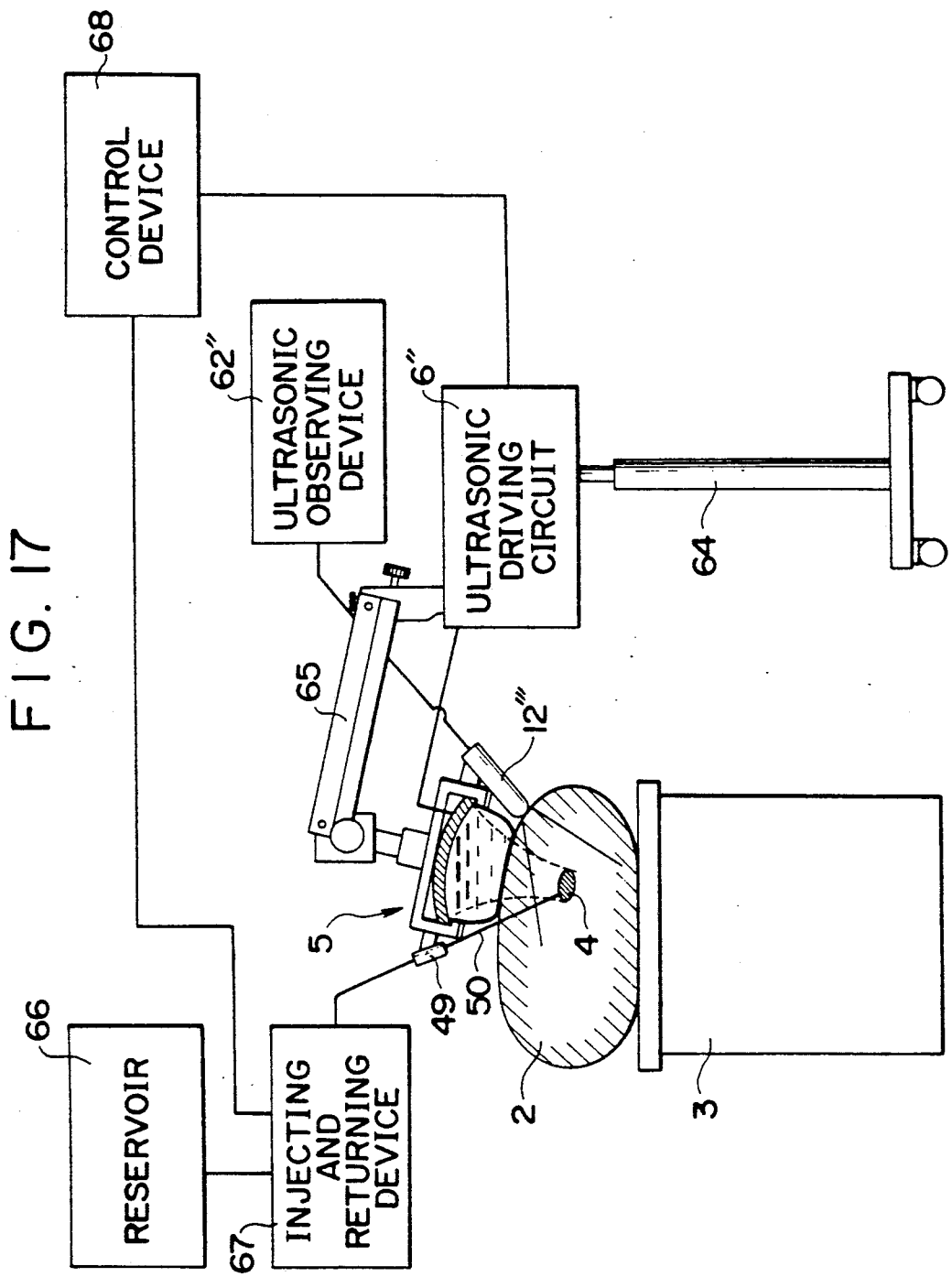
FIG. 17 is a schematic view showing an eighth embodiment of an ultrasonic treatment system of the present invention.

Referring now to FIG. 17, there is shown an eighth embodiment of the present invention. An ultrasonic wave generator 5' is supported by a support arm 65 mounted on the upper part of a support stand 64 so that the ultrasonic waves are converged to a part 4 to be treated through a water bag 7. The generator 5' can be positioned at a desired attitude and position by the support arm. A guiding means 49 for guiding a piercing needle 50 and an ultrasonic probe 12''' for observing the inside of a body are mounted around the generator 5'. The guiding means 49 guides to a part 4 to be treated treatment instruments such as a piercing needle or catheter which introduces and returns the medical liquid in a reservoir 66 to and from the part 4 to be treated. An injecting and returning device 67, an ultrasonic observing device 62''' and an ultrasonic driving circuit 6'' are controlled in such a manner that a treatment suitable for the condition of the part 4 to be treated can be conducted.

Figure 18:
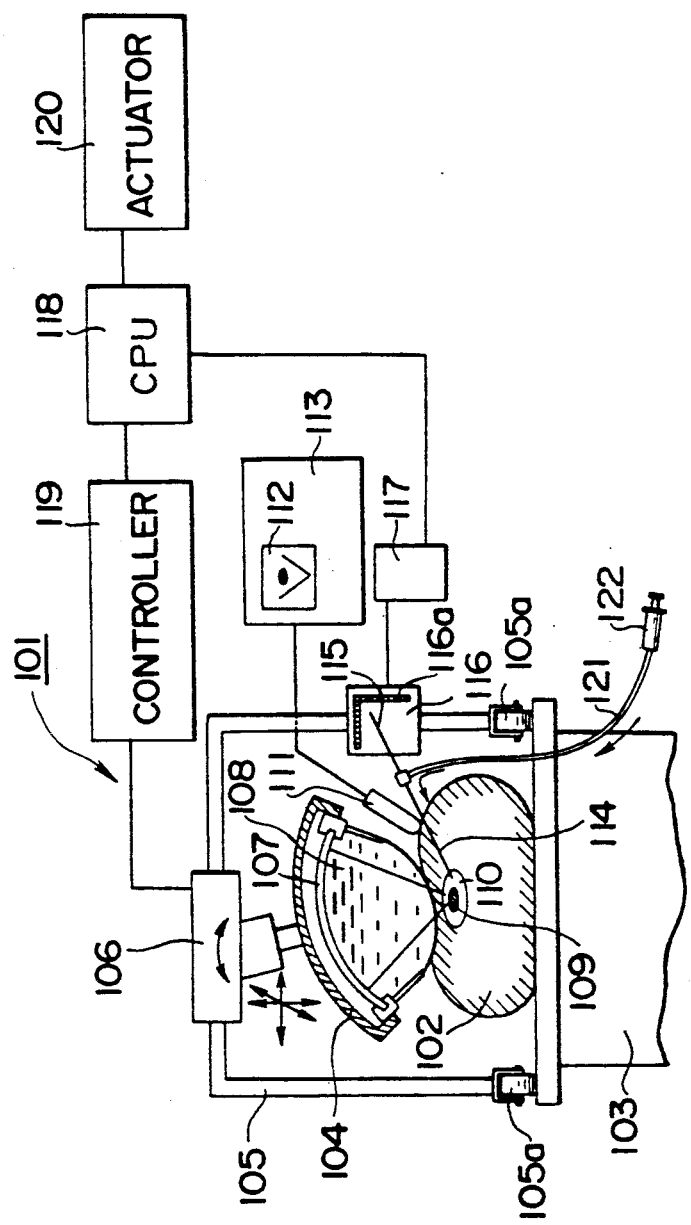
FIG. 18 is a schematic view showing a ninth embodiment of an ultrasonic treatment system of the present invention.

Referring now to FIG. 18, there is shown a ninth embodiment of the present invention. An ultrasonic treatment system 101 includes an ultrasonic wave generator 104 which is movably disposed upon a therapeutic bed 103 on which a human body 102 rests. The generator 104 is supported from a moving device 106 movably mounted on a carriage 105 which is movably in a direction perpendicular to the plane of the drawing sheet by casters 105a on the bed 103 so that it can be moved in three-dimensional direction.

The ultrasonic generator 104 comprises an ultrasonic oscillating element 107 and a water bag 108 filled with an ultrasonic wave transmitting medium such as water, which is disposed in front of the element 107. The water bag 108 is in contact with the surface of the human body 102. An ultrasonic probe 111 located outside of the body is used for observing the inside of the body 102, such as calculus 109 and the like in the cholecyst 110. An observing device 113 including a monitor device 112 is connected to the ultrasonic probe 111.

On the other hand, a piercing needle 114 for injecting a lithotriptic, calculus dissolving agent is caused to pierce the skin under observation of the ultrasonic probe 111 so that the tip end of the needle is located near the cholecyst having the calculus 109 therein. The piercing needle 114 is integrally provided with a position indicating pointer 115 at the base end thereof. The tip end of the pointer 115 faces a graduation index secured to the carriage 105. The information on the position of the tip end of the piercing needle 114 (that is, the position of the cholecyst) is fed to a CPU 118 via a positional sensor 117 which detects the index position pointed by the pointer 115. Three dimentional movement of the generator 104 is carried out by the moving device 106 in response to a control signal fed to the moving device 106 via a controller 119 from the CPU 118. An actuator 120 is connected to the CPU 118. A lithotriptic injecting syringe 122 is connected to the base of the piercing needle 114 via a tube 121. Although the description of devices which supply power for generating ultrasonic waves is omitted, these devices are controlled by CPU 118 and controller 119.

The ultrasonic treatment system of the present embodiment will operate as follows. The generator 104 is moved by the carriage 105 and the moving device 106 in such a manner that the underside of the water bag 7 is in contact with the upper surface of the human body 102 lain on the bed 103 as shown in FIG. 18. Then the piercing needle 114 is caused to pierce the cholecyst 110 having calculus 109 therein under observation by the ultrasonic probe 111. Lithotriptic is injected into the cholecyst 110 through the syringe 114. Information on the position of the tip end of the piercing needle 114 is fed to the CPU 118 via the indication pointer 115 and the positional sensor 117. Upon basis of the positional information, the CPU 118 sends a control signal via the controller 119 to the moving device 106 for moving the generator 104 so that the ultrasonic waves are suitably converged to the calculus 109. Accordingly, irradiation of the calculus 109 with ultrasonic waves from the generator 104 promotes the dissolution of the calculus 109 with the lithotriptic. The therapeutic effect can be remarkably improved.

If the calculus is shifted, tracking of the tip end of the piercing needle 114 to the calculus 109 makes it possible to conduct automatic tracking of the generator 104 since the amount of movement of the needle 114 is detected by the positional sensor 117 to operate the moving device 104 via the CPU 118 and the controller 119.

Figure 19:
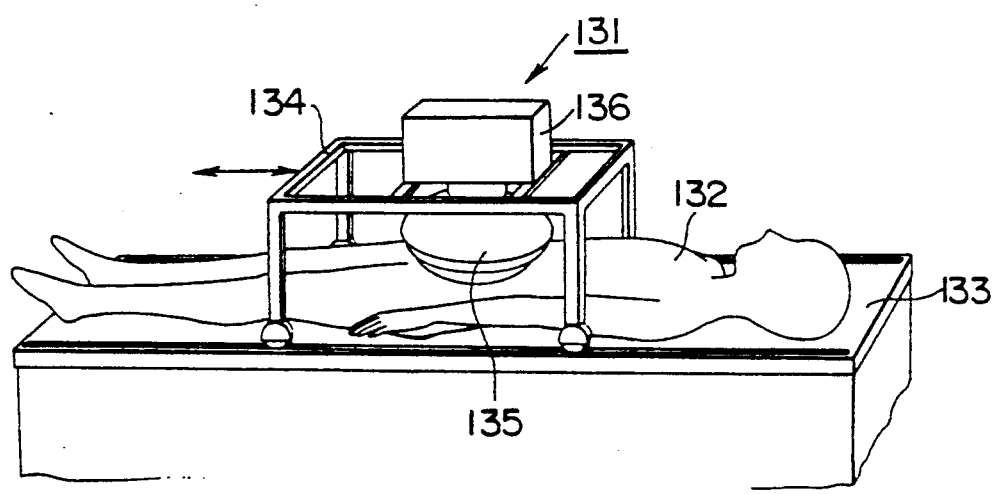
FIG. 19 is a schematic view showing a tenth embodiment of an ultrasonic treatment system of the present invention.
Figure 20:
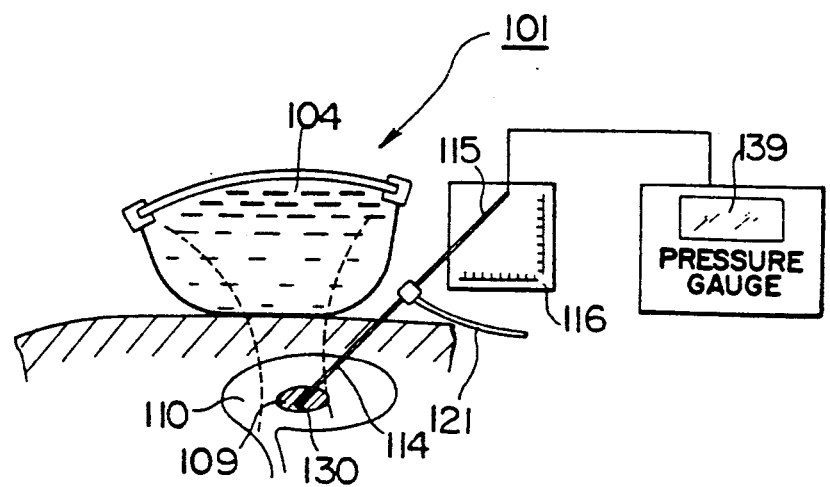
FIG. 20 is a schematic view showing an example of means for confirming the position of a piercing needle for introducing a lithotriptic.

Referring now to FIG. 19, there is shown a tenth embodiment of the present invention. An ultrasonic treatment system 131 includes a unit 136 comprising the ultrasonic wave generator 104, the carriage 105, the moving device 106, the indicating pointer 115, and the positional sensor 117 which are used in the system 101 of FIG. 18. That is, in the ultrasonic treatment system 131, a four leg carriage 134 which is movable in a longitudinal direction is disposed on the both sides of the upper face of the therapeutic bed on which a human body rests. The unit 136 in which the ultrasonic wave generator 135, the moving device for the generator and the piercing needle position detector are incorporated is supported on the carriage 134.

In the thus formed ultrasonic treatment system 131, the piercing needle is caused to pierce a part to be treated upon basis of the ultrasonic tomographic image and lithotriptic is injected thereto as similarily to the system 101 shown in FIG. 18. Thereafter, the position of the indicating pointer is picked up by the sensor at the piercing needle position measuring portion and the signal is received by CPU where coordinates to which the needle is to be moved are computed. The carriage 134 is moved upon basis of the information on the position from the piercing needle position detector so that the underside of the water bag of the generator 135 is positioned upon the surface of the body 131 corresponding to the part to be treated. The focussing of the generator 131 is conducted. Then the part to be treated is irradiated with ultrasonic waves to destroy the calculus.

The whole of the system 131 is compact in size and the easiness of operation of the system 131 is remarkably improved.

In order to confirm whether or not the tip end of the piercing needle 14 is located in the vicinity of the calculus 109, there is provided a pressure sensor 130 which detects the pressure formed by treatment ultrasonic beam at the tip end of the piercing needle 114 to conduct position control. That is, when the output from the pressure sensor 130 is higher than a given value, this represents that the ultrasonic beam is incident upon the vicinity of the calculus 109. When the output is lower than the given value, this represents that the beam misses the calculus. At this time, the ultrasonic generator is moved by the moving device shown in the above mentioned embodiments to carry out the position compensation.

In this case, an operator may manually move the moving device (not shown) while looking at the reading of a pressure gauze 139. Alternatively, automatic tracking may be conducted in response to a signal from a CPU which receives the pressure value.

Figure 21:
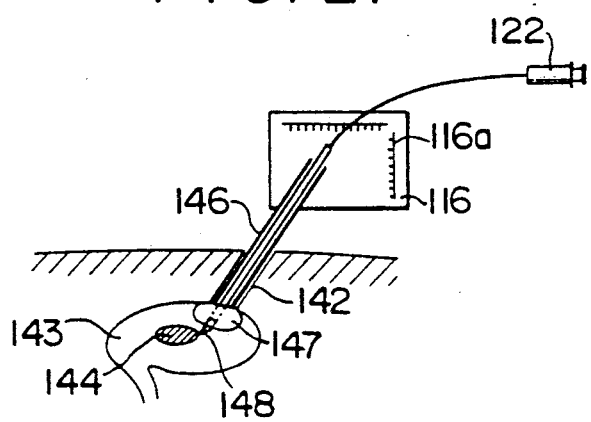
FIG. 21 is a schematic view showing an example in which a balloon catheter is used as a lithotriptic introducing piercing needle.

The treatment using only a piercing needle is unstable. There is a fear that the tip end of the needle will be shifted from an initial position. In this case, a sheath 146 is penetrated through a burrow 142 toward a calculus 144 in the cholecyst 143 as shown in FIG. 21. A balloon catheter 146 for injecting a medical liquid is inserted into the sheath 146. The catheter is fixed in position by inflating the balloon. Measuring of the position detects the movement of the sheath 146. Reference numeral 148 depicts a pressure sensor.

Figure 22:
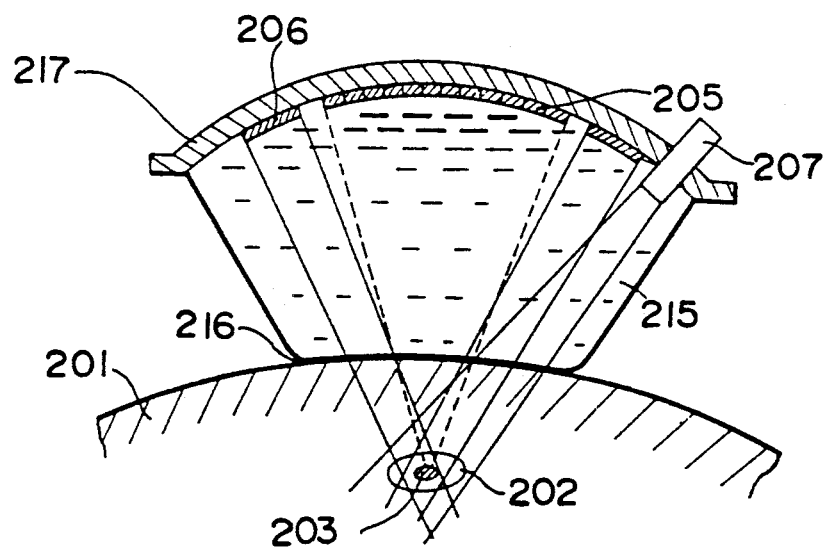
FIG. 22 is a sectional view showing an eleventh embodiment of an ultrasonic treatment system of the present invention.
Figure 23:
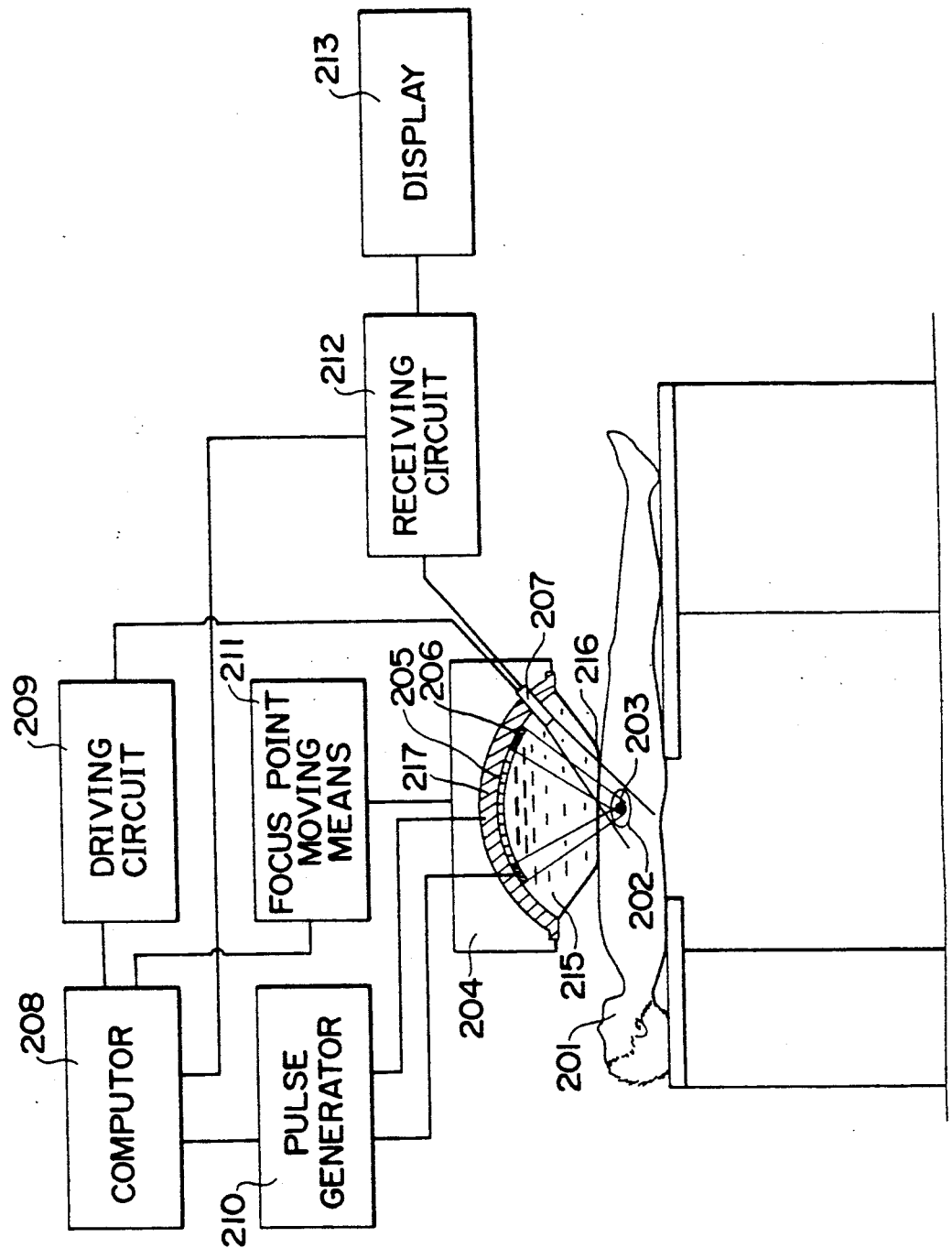
FIG. 23 is a schematic view showing a whole structure of the ultrasonic treatment system shown in FIG. 22.

Referring now to FIGS. 22 and 23, there is shown an eleventh embodiment of an ultrasonic treatment system of the present invention. Reference numerals 201, 202 and 203 depict a human body, a cholecyst and a calculus in a body, respectively. Although the present embodiment is shown for treating the calculus in the cholecyst, it is apparent that the present invention is not limited to this treatment.

This ultrasonic treatment system comprises means for detecting the position of a calculus in a body, a first ultrasonic wave irradiating means for destroying the calculus and the like, a second ultrasonic wave irradiating means for dissolving the calculus and the like and means for moving a focus of ultrasonic waves.

The position detecting means and the first and second ultrasonic irradiating means are mounted upon the inner side of a partial spherical shell 217. The position detecting means comprises an ultrasonic transducer 207 at an end of the partial spherical shell 217 for obtaining a tomographic image of a part to be treated where a calculus and the like exist in a body, a driving circuit 209 for driving the ultrasonic transducer 207, a receiving circuit 212 for processing a signal from the part to be treated detected by the ultrasonic transducer 207, and a display device 213 which displays the signal processed by the circuit 212 on CRT. The first ultrasonic wave irradiator 205 which transmits an ultrasonic beam for destroying the calculus in the body comprises a multiplicity of piezoelectric oscillating elements juxtaposed in a mosaic manner on the inner side of the element holder of the spherical shell 217. As is similar to the first ultrasonic irradiator 205, the second ultrasonic irradiator 206 which transmits an ultrasonic beam for promoting to dissolve the calculus in the body also comprises a multiplicity of piezoelectric oscillating elements juxtaposed in a mosaic manner on the inner side of the element holder of the spherical shell 217. Both first and second ultrasonic irradiators 205 and 206 are connected to a pulse generator 210 for driving the irradiators. The ultrasonic oscillating elements of the first ultrasonic irradiator 205 generate 300 KHz to 2 MHz ultrasonic wave beam to destroy the calculus 203 and the ultrasonic oscillating elements of the second ultrasonic irradiator 206 generate 10 KHz to 500 KHz ultrasonic beam to promote the dissolution of the calculus.

The focus moving means 211 moves the support 204 to converge the ultrasonic beam from the first and second irradiators 205 and 206 at the calculus 203 in the body. The moving means 211 is connected to a computor 208 together with the pulse generator 210 and the driving circuit 209. The computor 208 is connected to the driving circuit 209, the pulse generator 210, the focus moving means 211 and the receiving circuit, etc. for controlling the same. The partial spherical shell 217 having the first irradiator 205, the second irradiator 206 and the ultrasonic wave transducer 207 is covered with a water bag 216 of a soft resin material at the surface thereof. The water bag 216 is filled with an ultrasonic transmitting medium 215 such as water. The outer surface of the water bag 216 is in close contact with the human body 201.

Operation of the ultrasonic treatment system of the present embodiment will be described. Firstly lithotriptic is injected to the cholecyst 202 by means of syringe and the like through an endoscope or skin prior to treating the calculus in the cholecyst 202 in the body 201. Then the computor 208 feeds a signal to the driving circuit 209 to drive the same. A driving signal is fed to the ultrasonic transducer 207. The ultrasonic transducer 207 detects an ultrasonic echo from a position near the cholecyst 202 in the body 201. The detected echo signal is fed to the receiving circuit 212 which processes the detected echo signals to display a tomographic image near the cholecyst 202 on the display device 213 and feeds a position signal of the calculus 203 to the computor 208. The computor 208 compares the fed position signal of the calculus 203 with the focus position of the first irradiator 205. If both positions do not coincide with each other, the computor 208 feeds a signal to a focus moving means 211 to drive it for moving the support 207 so that the position of the calculus 203 coincides with the focus of the first ultrasonic irradiator 205. When both positions coincide with each other, the computor 208 feeds a signal to the pulse generator 210 to drive it so that the generator 210 provides a driving pulse to the first ultrasonic wave irradiator 205. An ultrasonic wave beam is generated from the first irradiator 205. The beam is converged to a thin beam having a narrow width at the calculus 203 in the cholecyst 202 in the body 201 through the water bag 216 filled with the ultrasonic wave transmitting liquid 215 to destroy the calculus 203. The destroy condition of the calculus 203 is observed from the tomographic image displayed on the display device 213 by the ultrasonic transducer 207. Accordingly, an operator determines whether or not an ultrasonic beam for promoting the calculus dissolution is necessary while observing the destroy condition of the calculus 203. If the operator determines that a beam is necessary, he commands the computor 208 to irradiate the calculus 203 with the ultrasonic beam for promoting the calculus dissolution. The computor 208 feeds a signal to the pulse generator 210 in response to the command. The pulse generator 210 provides the second ultrasonic generator 206 with a driving pulse to irradiate the calculus 203 with an ultrasonic beam for promoting the dissolution of the calculus 203. This ultrasonic beam has a wide width and oscillates the gall and the lithotriptic in the cholecyst 202 in the body via the ultrasonic wave transmitting medium liquid 215 and the water bag 216 to dissolve the calculus 203. The dissolution condition of the calculus 203 is obtained from the ultrasonic transducer 207 and may be observed from the tomographic image displayed on the display device 213. Accordingly, the operator determines whether or not the treatment should be terminated while observing the dissolution of the calculus 203 from the tomographic image. When the treatment should be terminated, the operator commands the computor to terminate the treatment. In response to the command, the computor 208 sends a driving termination signal to the pulse generator 210. Then the pulse generator 210 terminates sending driving pulses to the first and second ultrasonic irradiators 205 and 206. This terminates the treatment.

Although the ultrasonic beam for promoting the dissolution of the calculus 203 is generated after the ultrasonic beam for destroying the calculus 203 has been generated in the eleventh embodiment, the ultrasonic beam for destroying the calculus 203 may be generated simultaneously with the ultrasonic beam to promote the dissolution of the calculus 203 or both ultrasonic beams may be alternately generated.

Since destruction of the calculus, etc. can be carried out simultaneously with the dissolution of the calculus in the present embodiment in such a manner, a complication, such as choloplania, due to clogging of body cavity or canal with destroyed calculi will not occur, resulting in a reliable and safe treatment.

Figure 24:
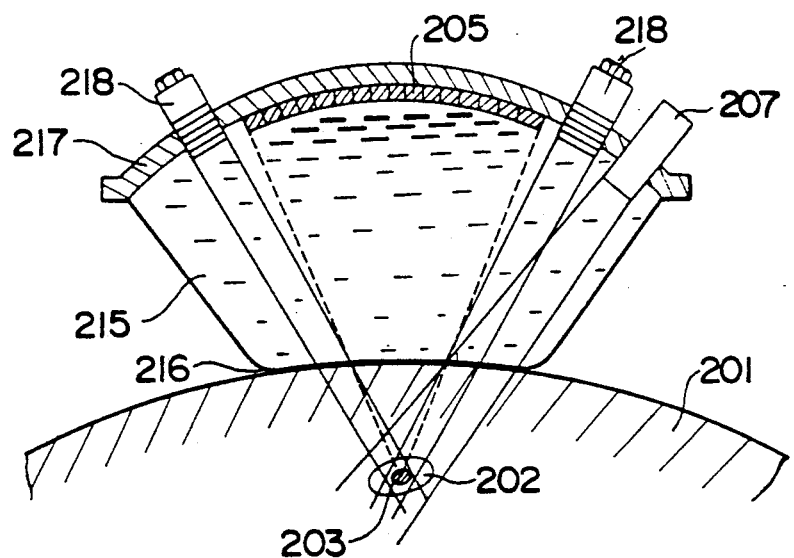
FIG. 24 is a sectional view showing a twelfth embodiment of an ultrasonic treatment system of the present invention.

Referring now to FIG. 24, there is shown a twelfth embodiment of an ultrasonic treatment system of the present invention. Since the present system is substantially identical with the ultrasonic treatment system of FIG. 22 excepting a second ultrasonic irradiator 206, like numerals depict like parts and the description of them will be omitted.

The second ultrasonic irradiator 206 in the ultrasonic treatment system in FIG. 22 comprises a multiplicity of piezoelectric elements while the second ultrasonic irradiator in the present embodiment of the treatment system comprises Langevin type oscillating element 218 which generates 100 KHz wide width ultrasonic beam. Since the function of the second ultrasonic irradiator 218 of the present embodiment is identical with the second ultrasonic irradiator 206 of the ultrasonic treatment system of FIG. 22, it is apparent that the present embodiment operates similarly to the eleventh embodiment.

Figure 25:
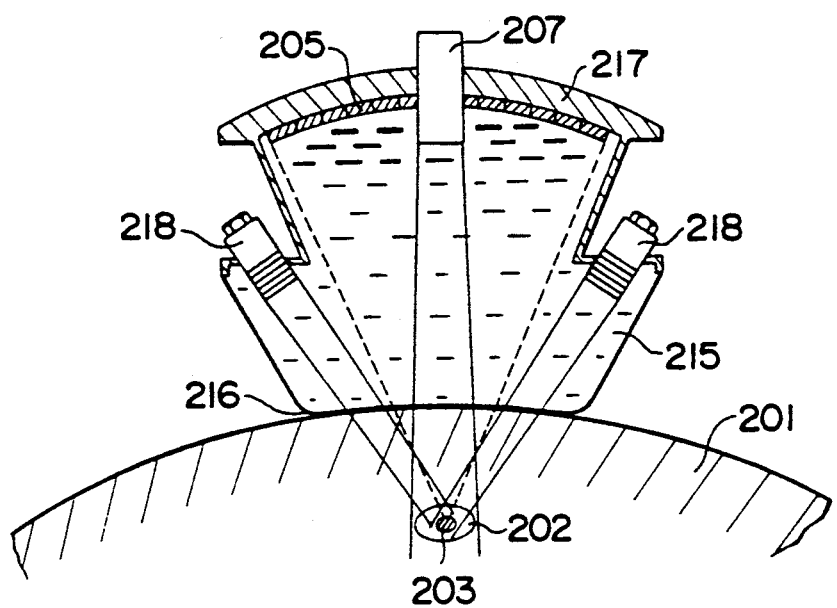
FIG. 25 is a schematic view showing a thirteenth embodiment of an ultrasonic treatment system of the present invention.

Referring now to FIG. 25 there is shown a thirteenth embodiment of an ultrasonic treatment system of the present invention. This embodiment is substantially identical with the twelfth embodiment shown in FIG. 24 excepting that the Langevin type oscillating element 218 which is used as the second irradiator in the system of FIG. 24 is mounted on the partial spherical part of the spherical shell 217 while this second irradiator of the embodiment is disposed at a position nearer to the human body 201 than the partial spherical part of the spherical shell. Such structure makes it possible to provide a compact system without changing the operation and effect.

Figure 26:
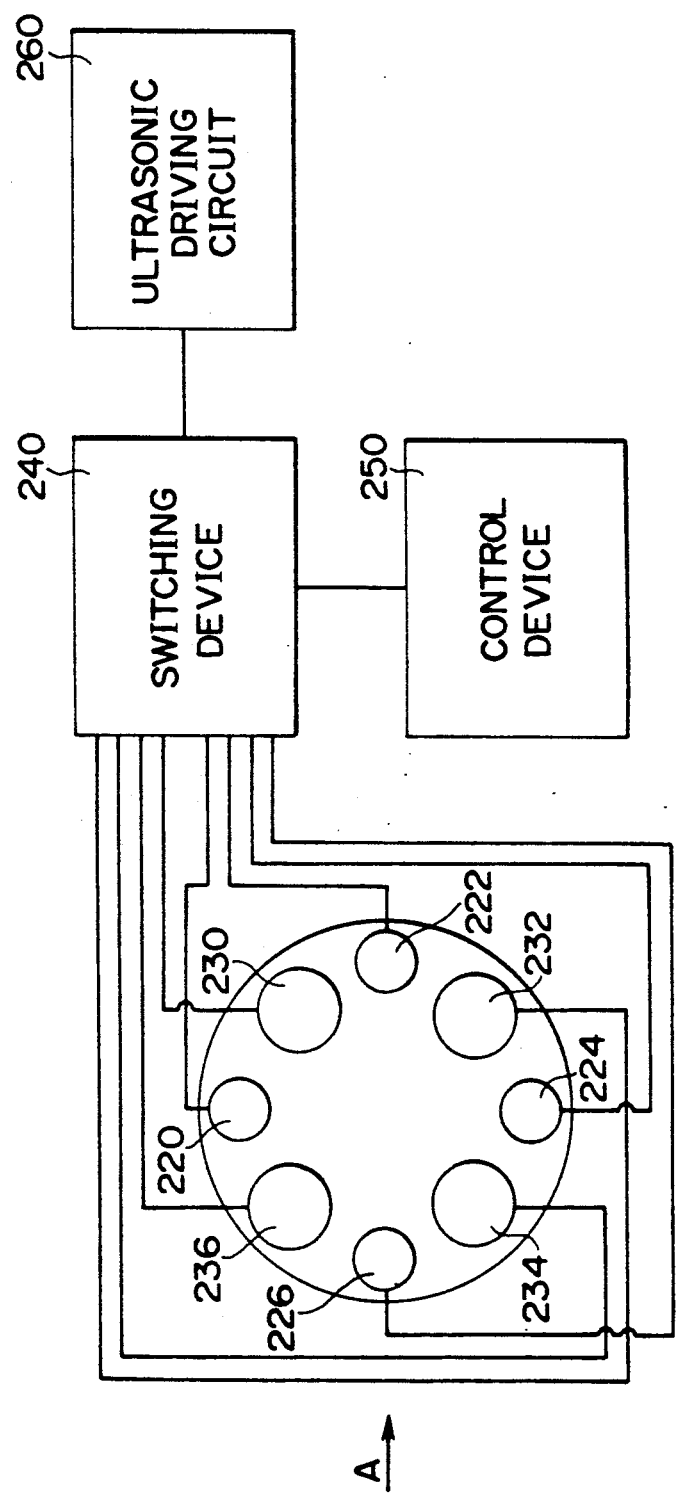
FIG. 26 is a schematic view of a fourteenth embodiment of an ultrasonic treatment system of the present invention.

Referring now to FIG. 26, there is shown a fourteenth embodiment of an ultrasonic treatment system in which first ultrasonic irradiators 220, 222, 224 and 226 and second ultrasonic irradiators 230, 232, 234 and 236 are disposed in a random or alternate manner.

One or more of the first and second ultrasonic irradiators are selectively operated by means of switching device 240. That is, an output from an ultrasonic driving circuit 260 is distributed to any of oscillating elements by means of switching device 240. Switching is controlled by the control device 250.

One or more of the first ultrasonic irradiators 220, 222, 224, 226 generate 300 KHz to 2 MHz ultrasonic waves for destroying a calculus and one or more of the second ultrasonic irradiators generate 10 KHz to 500 KHz ultrasonic waves for promoting the dissolution of the calculus.

Although not shown, the ultrasonic irradiator is not always disposed on the same concave member, only the second ultrasonic irradiator may be disposed at a position nearer to the human body.

Figure 27:
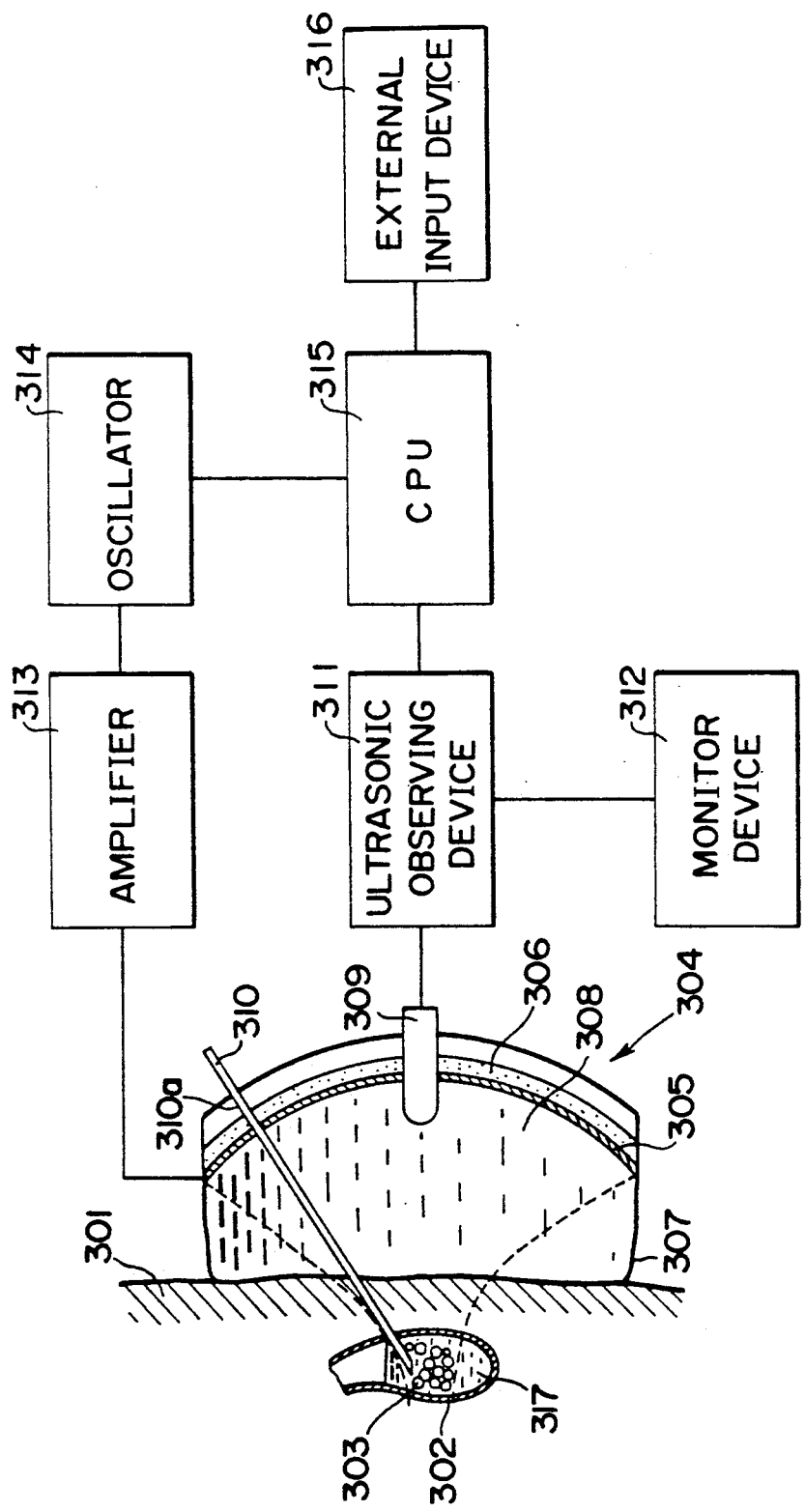
FIG. 27 is a view of a fifteenth embodiment of the present invention in which section of a main part of an ultrasonic treatment system is shown.

Referring now to FIG. 27, there is shown a fifteenth embodiment of an ultrasonic treatment system of the present invention for treating the calculus, an object to be treated which is formed in the cholecyst in a human body. Reference numeral 301 depicts a human body, 301 a cholecyst in the human body, 303 a calculus, a target to be treated, formed in the cholecyst 302, 304 an ultrasonic wave generator which opposes the calculus 303, 305 an ultrasonic wave oscillating element comprising a partial spherical piezoelectric element disposed on the inner side of the ultrasonic wave generator 304, and 306 a dumping layer on the rear side of the oscillating element 705 for expanding a driving frequency range. The dumping layer 306 is formed of epoxy resin mixed with tungsten powder. A water bag 307 which covers the front of the ultrasonic wave generator 304 is filled with an ultrasonic wave transmitting liquid 308 such as water for transmitting ultrasonic wave to a living body. A well known mechanical scan type ultrasonic probe 309 is provided at the center of the ultrasonic wave generator 304. A closable hole 310a into which a syringe needle 310 for injecting a lithotriptic if needed is provided on a part of outer periphery of the generator 304. The ultrasonic probe 309 is connected to an ultrasonic observing device 311, which is connected to a monitor device 312.

On the other hand, the ultrasonic oscillating element 305 is connected to an amplifier 313, which is connected to an oscillator 314. The oscillator 314 and the ultrasonic observing device 311 are connected to a CPU 315, to which an external input device 316 is connected.

Operation of the thus formed ultrasonic treatment system will be described which is used for the treatment of the calculus 303 in the cholecyst 302 in the human body 301.

Firstly, the water bag 307 is brought into intimate contact with the surface of the human body 301 so that the ultrasonic wave generator 304 of the present ultrasonic treatment system is opposed to the calculus 303 in the human body 301. The position of the calculus 303 is confirmed by the ultrasonic probe 309. Size, number and forming condition, etc. is detected by the monitor device 312. A syringe needle 310 is then caused to pierce the cholesyst 302 through a hole 310 of the ultrasonic wave generator 304.

A biliary calculus dissolving agent 317, for example methyl-tertiary-butyl-ether, abbreviated as M. T. B. E) is injected into the cholecyst 302. The calculus 303 is irradiated with ultrasonic wave to promote the dissolving effect of the biliary calculus dissolving agent 317 for treating the calculus 303. At this time, irradiation of the calculus with the ultrasonic wave is conducted in a most effective manner to dissolve the calculus depending upon the size and existing condition of the calculus 303 in the present ultrasonic treatment system. That is, if a number of small calculi are present in the cholecyst 302, the ultrasonic beam is brought into out-of-focus, that is, the diameter of the convergence of the ultrasonic wave is made larger at the point of focus so that ultrasonic waves are caused to impinge upon a number of the dotted calculi simultaneously to effectively dissolve the calculi. If there are 2 or 3 relatively large calculi, the ultrasonic waves are converged into a small spot to irradiate each one of small number of calculi. If the number of calculi is decreased on treatment, the convergence of the ultrasonic wave is gradually changed so that the whole of the calculi are properly irradiated with ultrasonic wave.

In order to most effectively change the convergence of the ultrasonic waves depending on the size of calculi and the formation condition in such a manner, the driving frequency generated by the oscillator 314 which is connected to the ultrasonic oscillating element 305 is changed. The reason why change in driving frequency of the ultrasonic oscillating element changes the convergence of the generated ultrasonic wave will be described.

Let the half value width at the point of focus, that is, the sound pressure width at the focus which is a half of the maximum sound pressure, be denoted as b, where $$b = 1.42\lambda \frac{R}{D} \quad (1)$$

wherein
λ; wave length
R; curvature radius of a concave ultrasonic oscillating element
D; opening radius of a concave ultrasonic oscillating element
on the other hand, $$\lambda = \frac{c}{f} \quad (2)$$

wherein
c; sound velocity
f; driving fequency b is calculated by using formulae (1) and (2). For simplicity of calculation it is assumed that R=D, the an ultrasonic wave transmitting medium is water, the sound velocity is 1500 m/sec, the driving frequency f is 100 KHz and 1 MHz. b representative of convergence at the focus point is the 21 mm and 2.1 mm for f of 100 KHz and 1 MHz respectively under formulae (1) and (2). It is understood that the convergence varies 10 fold. If small calculi which are present in a wide area are dissolved by the irradiation of a wide converged ultrasonic wave, the driving frequency f is lowered to increase the outer spot diameter at a convergence point. If large calculi is to be dissolved, the driving frequency is made higher to converge the ultrasonic wave to each target for promoting the dissolution of the calculi.

In order to change the driving frequency of the ultrasonic oscillating element 305 of the oscillator 314, an instruction to change it should be sent to the oscillator 314. This is carried out by means of the external input device 316 including a key board and the like, the CPU 315 connected to the input device 316, the oscillator 314 and the amplifier 313. In other words, depending upon the size and aggregation condition of the calculi, necessary data is input to the external input device 316 to feed a signal to the oscillator 314 via the CPU 315. Although this operation is conducted by an operator, it is possible for the CPU 315 to feed data to the oscillator 314 upon basis of a predetermined program to change the driving frequency of the ultrasonic oscillating element 305 so that the convergence of the ultrasonic wave can be automatically changed. Such operation automatically changes the convergence to effectively conduct the dissolution of the calculi. The lithotriptic injected into the cholecyst 302 can be recovered by the syringe 310 after the dissolution has been accomplished.

Figure 28:
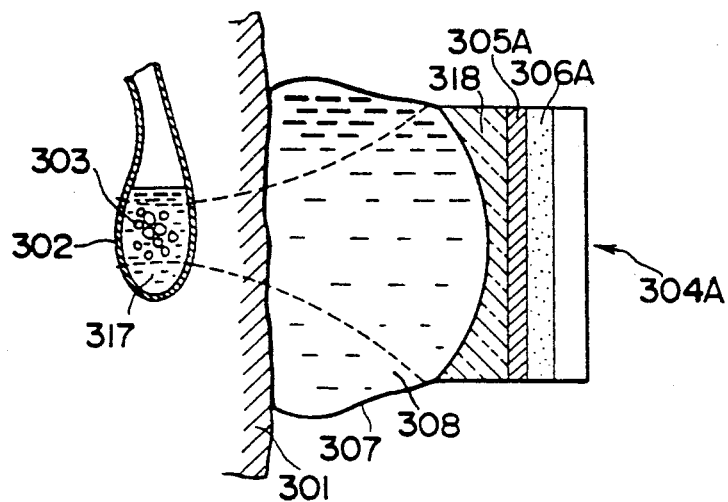
FIG. 28 is a sectional view showing a main part of the ultrasonic treatment system in the fifteenth embodiment.

Referring now to FIG. 28, there is shown a fifteenth embodiment of an ultrasonic treatment system for treating the calculus formed in the cholecyst. Since the ultrasonic treatment system of the present embodiment is substantially identical with the system shown in FIG. 27 in structure, like numerals depict like components and the description of same components will be omitted and only different components will be described.

An ultrasonic oscillating element 305A of an ultrasonic generator 304A in the ultrasonic treatment system in the present embodiment comprises a flat piezo-electric element. A converging lens 318 comprising a plano-concave lens converging the ultrasonic waves is applied to a front side of the generator from which ultrasonic waves are radiated. A dumping layer 306A is provided on the rear side of the ultrasonic oscillating element 305A as is similar to the element 305A of FIG. 27.

The convergence of the ultrasonic wave which is obtained by the flat ultrasonic oscillating element 305A and the lens 318 is suitably changed by changing the driving frequency of the ultrasonic oscillating element 305A. This is similar to the case of the ultrasonic treatment system in operation and effect. However the ultrasonic oscillating element 305A is very simple in structure in comparison with the concave ultrasonic oscillating element 305. Remarkable decrease in cost may be realized. For clarity of the drawing, an ultrasonic probe and syringe insertion hole are omitted from the ultrasonic generator 304 in the embodiment of the ultrasonic treatment system in FIG. 28.

Figure 29:
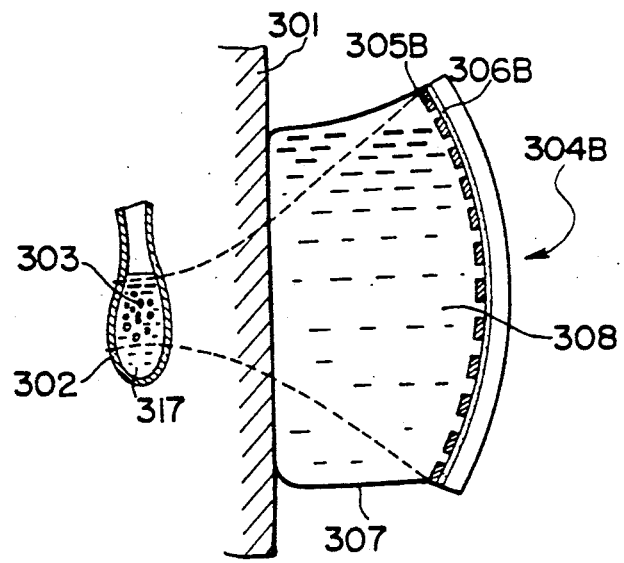
FIG. 29 is a sectional view showing a main part of a sixteenth embodiment of an ultrasonic treatment system.

Referring now to FIG. 29, there is shown a sixteenth embodiment of an ultrasonic treatment system. A ultrasonic wave generator 304B of the present ultrasonic treatment system is substantially identical with the ultrasonic generators 304 and 304 respectively shown in FIGS. 27 and 28 excepting that a number of ultrasonic oscillating elements 305B are mosaically disposed on the inner side of the spherical plate of the generator 305. A dumping layer 306B is disposed between the elements 305B and the plate. An ultrasonic probe and a syringe injection hole, etc. are also omitted in the present embodiment.

The ultrasonic treatment system of the thus formed present embodiment operates similarly to the ultrasonic treatment systems shown in FIGS. 27 and 28, and has the same effect.

Figure 30:
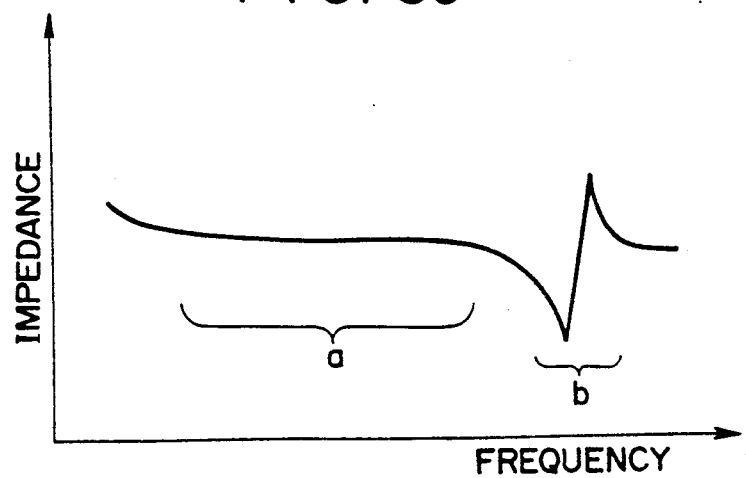
FIG. 30 is a graph showing the impedance characteristics of an ultrasonic oscillating element in an ultrasonic wave generator of the ultrasonic treatment system in the fifteenth and sixteenth embodiments.

Referring now to FIG. 30, there is shown a graph showing the impedance characteristics of an ultrasonic oscillating element used in the above-mentioned ultrasonic treatment system. The ordinate represents the impedance and the abscissa represents the driving frequency of an oscillating element. In FIG. 30, point b represents a point of resonance at which the ultrasonic oscillating element may be driven by a given driving frequency to generate ultrasonic waves. This means the band width of the driving frequency is narrow in the vicinity of the resonance point. Accordingly, this frequency range is not used in accordance with the present invention. Ultrasonic waves are generated in a driving frequency range in which the impedance is flat over a wide range. Thus, the dumping layers 306, 306A and 306B, etc. can be omitted. Initially the ultrasonic oscillating element may be formed of poly-vinylidene fluoride (P.D.D.), having a relatively wide driving frequency range.

Although the above embodiments have been described by limiting the object bo be treated to a calculus in the cholecyst, it is apparent that the present invention can be applicable to any calculus formed in the kidney and bladder as well.

A mechanism for injecting lithotriptic such as piercing needle disposed on the ultrasonic generator 304 may be separated from the generator 304.

Figure 31:
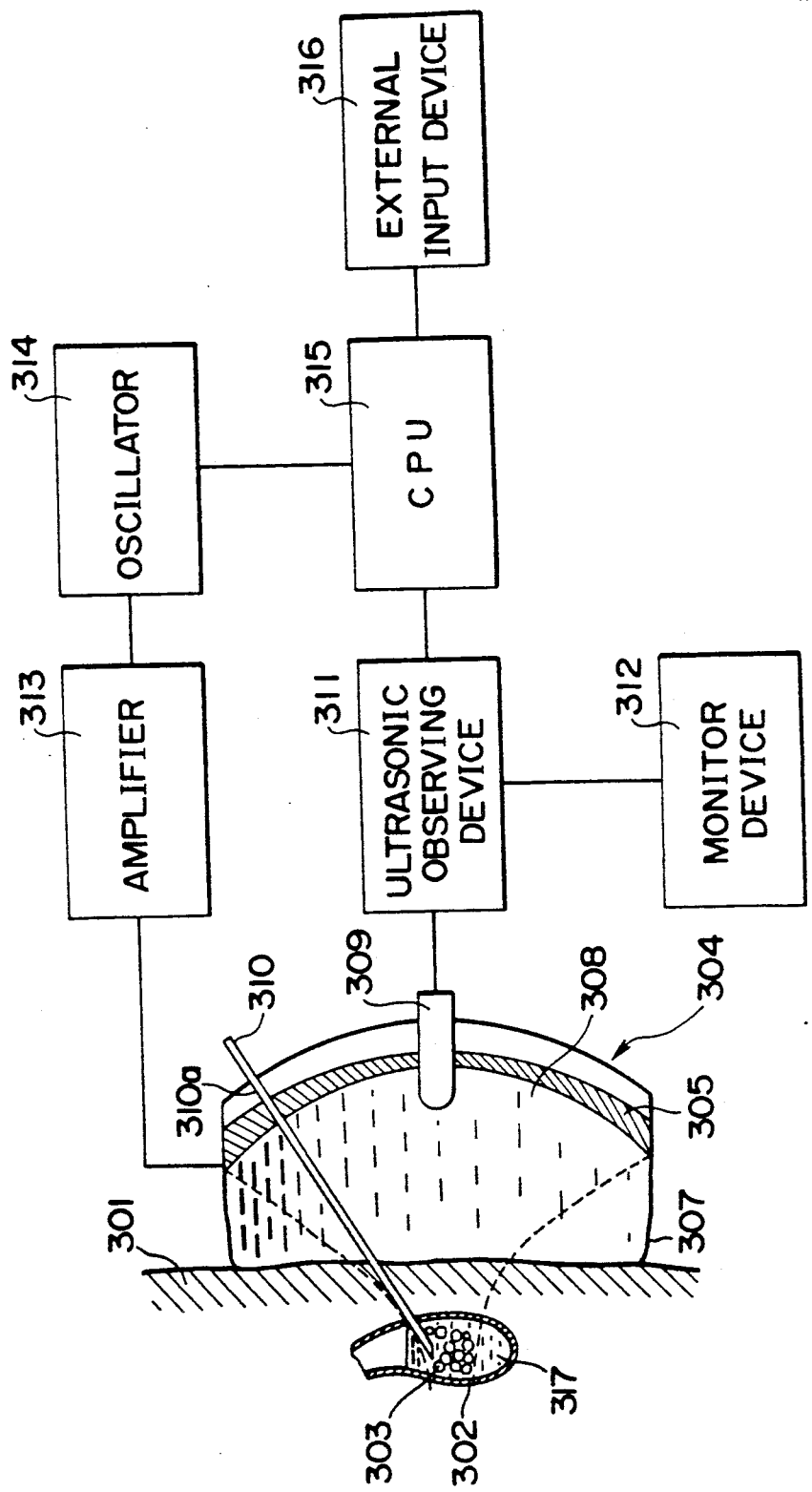
FIGS. 31 and 32 are views similar to FIG. 27 showing seventeenth and eighteenth embodiments respectively in which section of a main part of the ultrasonic treatment system is shown.
Figure 32:
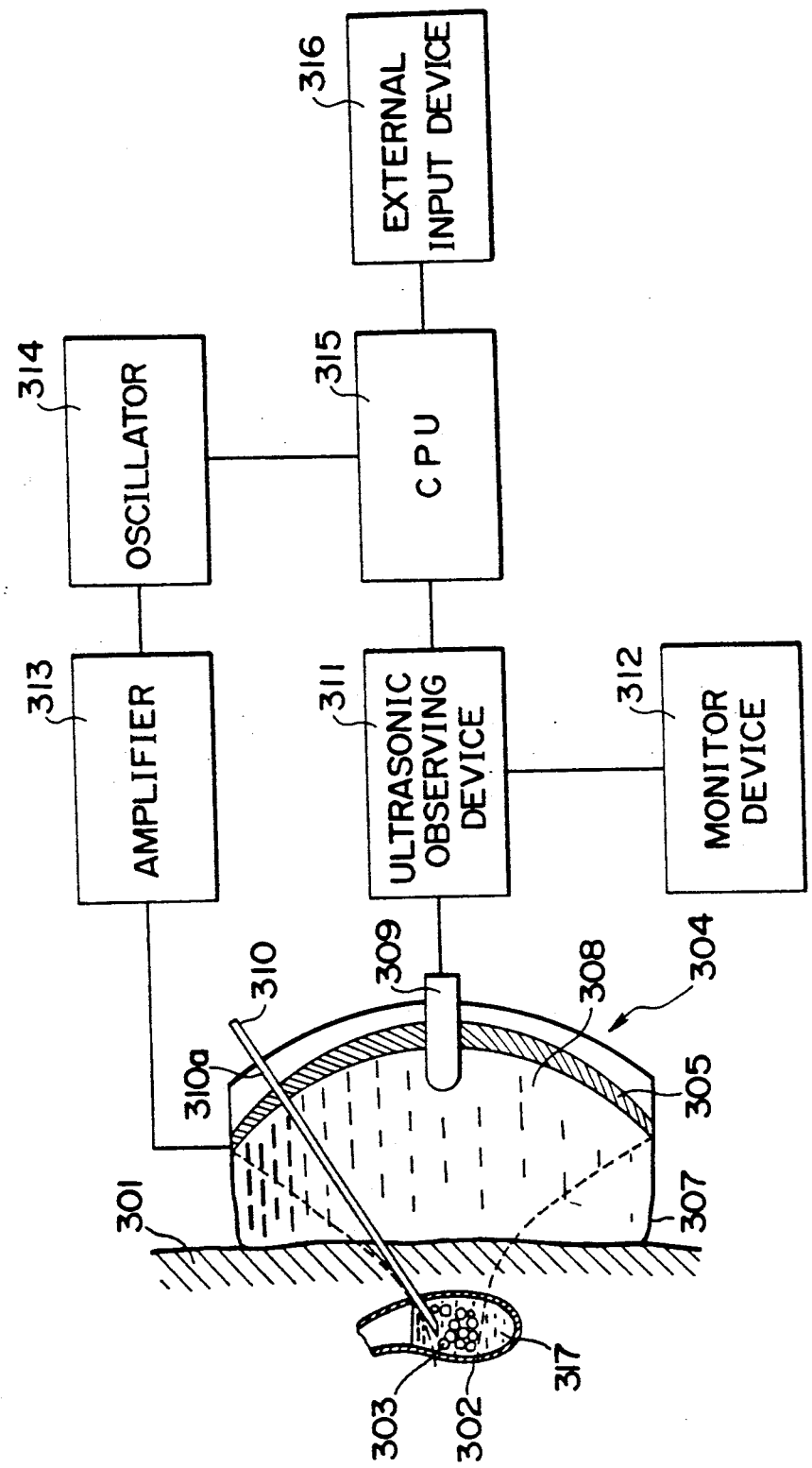

Referring now to FIGS. 31 and 32, there are shown seventeenth and eighteenth embodiments of ultrasonic treatment system of the present invention. The embodiments are substantially identical with the fifteenth embodiment shown in FIG. 27 excepting that the thickness of the ultrasonic oscillating element 305 is not constant. That is, the ultrasonic oscillating element 305 of FIG. 31 is thinner at the center thereof and thicker in the vicinity of the periphery. On the other hand, the ultrasonic oscillating element 305 of FIG. 32 is thicker at the center thereof and thinner in the vicinity of the periphery. This makes it possible for the generator to provide a plurality of points of resonance at which the impedance is low. That is, there are a plurality of points of resonance at which the element can be effectively driven. Accordingly the driving frequency can be changed over a wide range.

Further description of the seventeenth and eighteenth embodiments will be omitted since they are substantially identical with the fifteenth embodiment excepting the thickness of the oscillating element 305.

In accordance with the present invention, dissolution effect of the lithotriptic can be further promoted and fast and reliable treatment can be conduced by freely and simply controlling the convergence of the ultrasonic waves at a point of focus depending on the condition of calculus, on treatment of calculus formed in the body with a lithotriptic and irradiation with ultrasonic wave.

Figure 33:
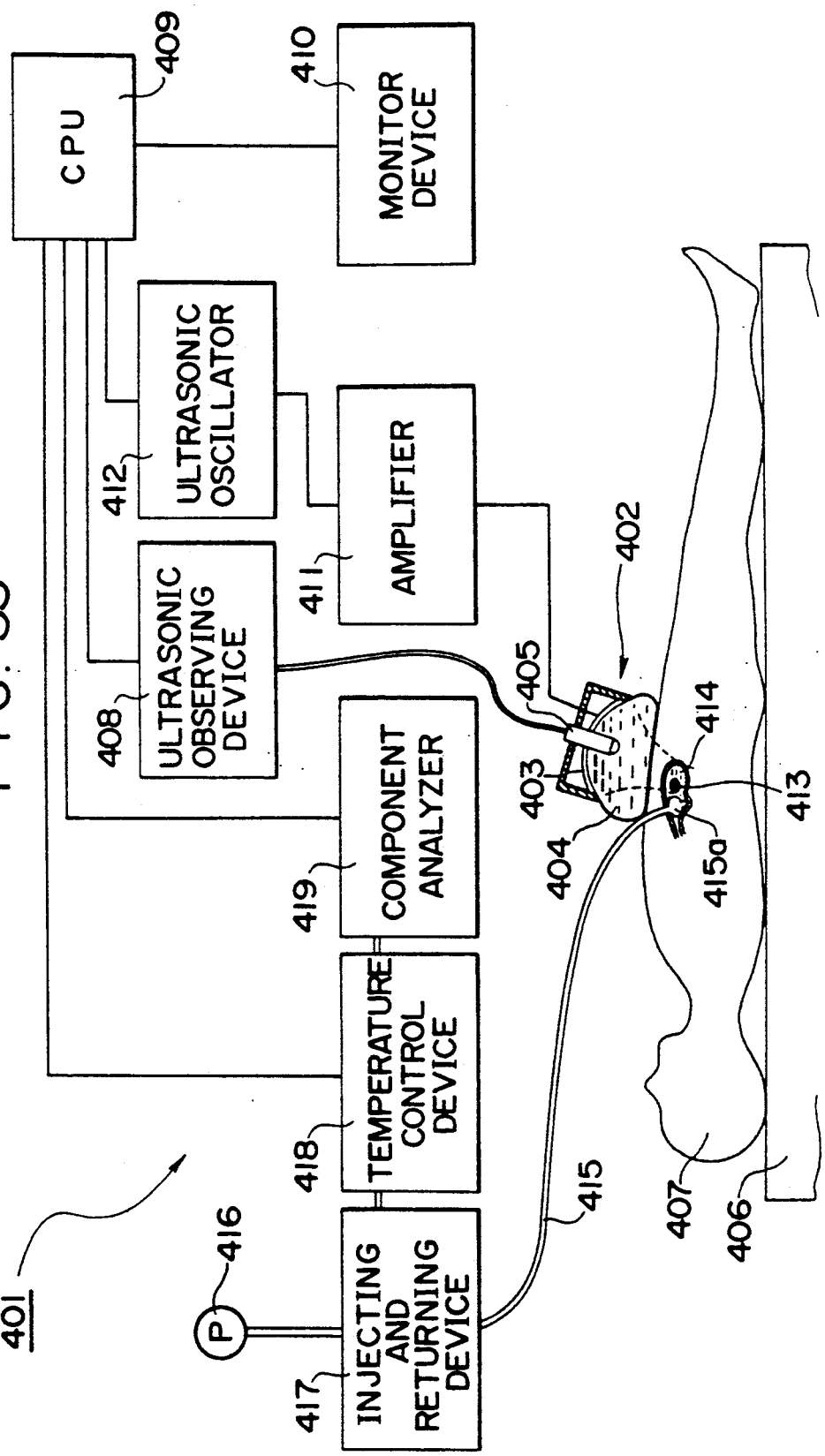
FIG. 33 is a schematic view showing a nineteenth embodiment of an ultrasonic treatment system.

Referring now to FIG. 33, there is shown a nineteenth embodiment of an ultrasonic calculus treatment system of the present invention. The calculus treatment system mainly comprises means for irradiating ultrasonic waves to promote the dissolution effect of a lithotriptic injected around a calculus, means for injecting the lithotriptic around the calculus, means for returning the injected lithotriptic and means for monitoring the effect of the lithotriptic.

An ultrasonic wave generator 402 which is an ultrasonic wave irradiating means comprises a concave ultrasonic oscillating element 403 including piezoelectric element such as PZT or the like and a water bag 404 made of a soft resin material and filled with an ultrasonic wave transmitting liquid which covers the front side of the oscillating element 403. An ultrasonic observing probe 405 is disposed at the center of the ultrasonic oscillating element 403.

The thus formed ultrasonic generator 402 is disposed in such a manner that the water bag 404 is in contact with the body surface opposed to a part to be treated in a human body lain on a therapeutic bed 406 as shown in FIG. 33 when the generator 402 is used. An ultrasonic probe 405 is connected to the ultrasonic observing device 408, which is then connected to a monitor device 410 via CPU 409. The ultrasonic oscillator 403 is also connected to the CPU 409 via an amplifier 411 and an oscillator 412. The cholecyst 414 in the body 407 in which a biliary calculus 413 is formed is pierced with the tip end of balloon catheter 415 through skin. The base part of the balloon catether 415 is connected to a lithotriptic injecting pump 416 via an injecting and returning device 417. The injecting and returning device 417 is connected to a temperature measuring and controlling device 418 and then to a lithotriptic component analyzer 419. These devices 418 and 419 are connected to the CPU 409.

Figure 34:
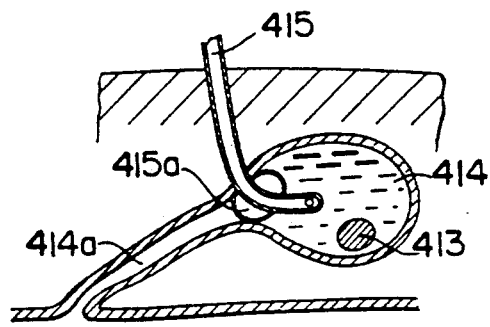
FIG. 34 is an enlarged sectional view showing a manner in which a lithotrite is used.

The calculus treatment system 401 the thus formed embodiment operates as follows. After the underside of the ultrasonic generator 402 of the water bag 404 is brought into contact with the surface of the body opposed to the biliary calculus 413 lain on the therapeutic bed 406, the biliary calculus 413 is detected by the observing ultrasonic probe 405 disposed in the ultrasonic generator 402 and the tip end of the balloon catheter 415 is caused to pierce the cholecyst 414 toward the calculus 413. Then a balloon 415a at the tip end of the balloon catheter 415 is inflated to clog the inlet 414a of the cholecyst 414 as shown in FIG. 34. Thereafter a lithotriptic is injected via the balloon catheter 415 by an injecting pump 416. If the inlet 414a of the cholecyst 414 is clogged with the balloon 415a, the injected lithotriptic can be prevented from flowing into the duodenum, etc. The lithotriptic is returned by the injecting and returning device 417 and the lithotriptic is controlled to have a given temperature and components by means of the temperature measuring and control device 418, the component analyzer 419 and the CPU 409. A driving voltage is applied to the ultrasonic oscillator 403 of the ultrasonic generator 402 from a oscillating circuit 412 via the amplifier 411. The ultrasonic waves are incident upon the biliary calculus 413 and the injected lithotriptic.

In the present embodiment of the calculus treatment system, the lithotriptic which is injected toward the calculus 413 is always controlled to have a given temperature and concentration and is recovered by means of injecting and returning device 417, temperature measuring and controlling device 418 and the component analyzer 419 is such a manner. In order to enhance the effect of the lithotriptic, the output power of the ultrasonic wave may be increased or the duration of irradiation time may be extended. However this increases the temperature of the area irradiated with the ultrasonic wave due to heat effect of the ultrasonic wave to give an adverse effect to a living body. Therefore the temperature of the lithotriptic is monitored so that a patient does not feel uncomfortable. The irradiation output of the ultrasonic wave is controlled so that the temperature of the lithotriptic will not exceeds a given value. Since optimum temperature at which the calculus is effectively dissolved changes depending upon the kinds of the calculus, the lithotriptic can be maintained to this optimum temperature. Excessively low temperature of the lithotriptic gives uncomfortability to a patient. This can be prevented by controlling the temperature of the lithotriptic.

Although the temperature measuring and controlling device 418 and the lithotriptic component analyzer 419 are provided as means for monitoring the effect of the lithotriptic in the above embodiment, the system may further include a device for detecting the flow rate of the lithotriptic and the amount of air bubble formed in the lithotriptic and the pressure in the cholecyst.

Since many of the lithotriptics have a relatively low boiling temperature and a high probability to evaporate on irradiation of ultrasonic wave, monitoring of temperature and air bubble can prevent the evaporation of lithotriptic to improve the safety to a living body.

The purpose of measuring the pressure in the cholecyst and the flow rate of the lithotriptic is to detect an abnormal condition such as clogging of a tube, or malfunction of a pump for the injecting and returning device while the lithotriptic is circulated. If such abnormal condition takes place, the pressure in the cholecyst is increased so that the lithotriptic overflows, resulting in leakage to other organs.

How much quantity of the biliary calculus 413 is dissolved can be measured by monitoring the pH and concentration and the components of the recovered lithotriptic. The quality (components) of the biliary calculus is firstly measured by X-rays and ultrasonic waves and the like. This is compared with the integrated output of the dissolved biliary calculus to determine the residual quantity of the calculus. The time until the temination of the treatment can be predicted from the time which was required to the current treatment.

Positioning of the ultrasonic wave generator 402, insertion of the balloon catheter 415 and injection of the lithotriptic into the cholecyst 414 can be monitored through the observing ultrasonic probe 405, ultrasonic observing device 408, the CPU 409 and the monitor device 410. Dissolution of the biliary calculus can be directly determined from the size of the biliary calculus. The amount of recovered lithotriptic can be properly controlled. If more recovery of the lithotriptic results in more of the effect, the recovered lithotriptic is increased. If recovery of the less lithotriptic gives the good result, the lithotriptic is recovered cyclically.

Figure 35:
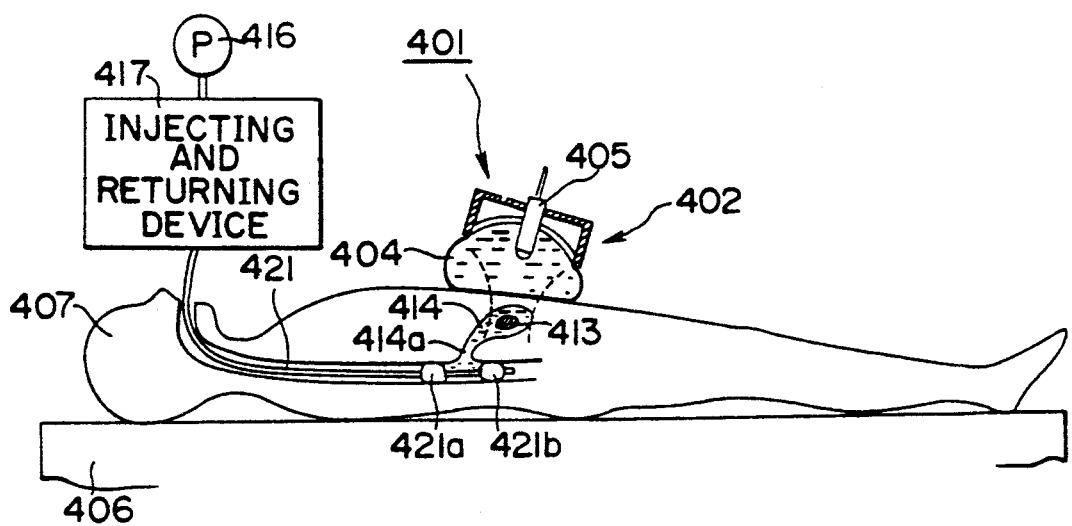
FIG. 35 is a schematic view showing the manner in which a balloon catheter different from that used in a lithotrite of FIG. 33 is used.

Referring now to FIG. 35, there is shown a case in which a balloon catheter different from that used in the lithotrite shown in FIG. 33 is inserted into the cholecyst through the mouth. Since the structure of the calculus treatment system 401 is substantially identical with that shown in FIG. 33, the description of it will be omitted. This balloon catheter 421 is a double balloon catheter which is provided with two balloons 421a and 421b at the tip end thereof. The balloons are extensible in an axial direction. The catheter 421 is inserted into a body cavity through the mouth so that an inlet of the cholecyst 414 is positioned between the two balloons 421a and 421b shown in FIG. 35. The balloons 421a and 421b are inflated to clogg the front and rear of the inlet 414 of the cholecyst 414. A lithotriptic is injected into the cholecyst 414 via a lithotriptic injection hole 421 pierced in the tube wall between the balloons 421a and 421b of the catheter 421 and the injected lithotriptic is returned by the injecting and returning device 417. The devices connected to the injecting and returning device 417 and the devices connected to the ultrasonic generator 402 shown in FIG. 33 are not shown, but of course are connected similarily as shown in FIG. 33.

Though the balloon catheter 421 is inserted into a body cavity through the mouth and the lithotriptic is injected and recoved, the system functions similarly to the case where the balloons catheter 415 is used and same effect is obtained. In this case a patient does not feel pain since the balloon catheter 421 is inserted through mouth.

Figure 36:
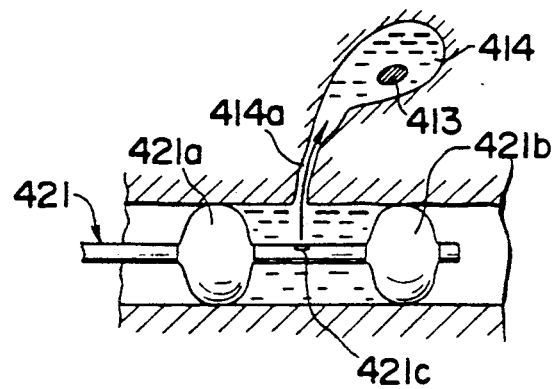
FIG. 36 is an enlarged sectional view showing a main part of the balloon catheter shown in FIG. 35.
Figure 37:
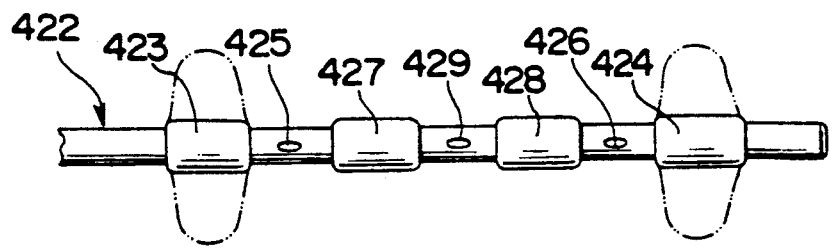
FIG. 37 is an elevational view showing another example of a balloon catheter used in a lithotrite.

Referring now to FIG. 37, there is shown a double balloon catheter to be inserted through the mouth, different from those shown in FIGS. 35 and 36. This balloon catheter 422 is provided with two clogging balloons 423 and 424 as is similar to the balloon catheter 421 shown in FIG. 36. The balloons are also extensible in an axial direction. Holes 425 and 426 for injecting and discharging the lithotriptic are formed on the tube wall of the balloon catheter in the vicinity of balloons 422 and 425 respectively so that the lithotriptic is forced to circulate through both holes 425 and 426. Two ultrasonic oscillating elements 427 and 428 of piezoelectric ceramics such as PZT(lead titanate zirconate). For imparting ultrasonic vibration to the injected lithotriptic are disposed on the outer periphery of the catheter between the holes 425 and 426. A sensor 429 for sensing the temperature, PH, concentration, etc are provided between the oscillating elements 427 and 428.

Since the physical properties of the lithotriptic injected and recovered can be directly recognized by thus formed balloon catheter 422, the effect of the injected lithotriptic on the calculus can be controlled in an optimum manner and the calculus treatment effect can be further improved. The present invention provides the following effects which have heretofore never been obtained.

(1) Lithotriptic, calculus dissolving agent can be circulated through a part to be treated while automatically maintaining the lithotriptic to optimum temperature and components.

(2) The treatment effect can be constantly monitored and the time until the treatment is terminated can be predicted.

(3) Lithotriptic can be easily injected into and recoved from a part to be treated through the mouth and skin by means of a balloon catheter.

(4) Lithotriptic can be automatically controlled in such a manner that it can be optimally used.

What is claimed is:

1. An ultrasonic treatment system for conducting treatment by converging ultrasonic waves which are generated outside of a body to a part to be treated in the body, comprising:

means for generating ultrasonic waves to be converged to the part to be treated, the ultrasonic generating means including a spherical shell having inner and outer surfaces, at least one ultrasonic generating element mounted on the inner surface, a water bag mounted on the inner surface, and a support member mounted on the outer surface;

means connected to the ultrasonic wave generating means for guiding a treatment instrument to the body, the guiding means being mounted on the support member in such a manner that the guiding means does not pass through the shell or the water bag and is movable with respect to the support member; and means connected to the support member for detachably holding an ultrasonic probe for use in determining the position of the part to be treated, the means for detachably holding the probe being connected to the support member so as to be movable with respect thereto.

2. An ultrasonic treatment system as defined in claim 1, further including means for visually observing the part to be treated.

3. An ultrasonic treatment system as defined in claim 2 in which the guiding means includes means for indicating the position of the treatment instrument.

* * * * *